(12) United States Patent
Ginsburg et al.

(10) Patent No.: US 9,750,585 B2
(45) Date of Patent: Sep. 5, 2017

(54) METHOD OF FABRICATING A DENTURE

(71) Applicant: Good Fit Technologies, Inc., Boston, MA (US)

(72) Inventors: Stephen Ginsburg, Wellesley, MA (US); Marc Ginsburg, Gloucester, MA (US)

(73) Assignee: GOOD FIT TECHNOLOGIES, INC., Boston, MA (US)

( * ) Notice: Subject to any disclaimer, the term of this patent is extended or adjusted under 35 U.S.C. 154(b) by 111 days.

(21) Appl. No.: 14/712,285

(22) Filed: May 14, 2015

(65) Prior Publication Data
US 2015/0327962 A1 Nov. 19, 2015

Related U.S. Application Data

(60) Provisional application No. 61/996,679, filed on May 14, 2014.

(51) Int. Cl.
| | |
|---|---|
| *A61C 13/10* | (2006.01) |
| *A61C 13/20* | (2006.01) |
| *A61C 13/36* | (2006.01) |
| *A61C 13/01* | (2006.01) |
| *A61C 13/00* | (2006.01) |
| *A61C 13/15* | (2006.01) |

(52) U.S. Cl.
CPC .......... *A61C 13/10* (2013.01); *A61C 13/0024* (2013.01); *A61C 13/01* (2013.01); *A61C 13/1016* (2013.01); *A61C 13/20* (2013.01); *A61C 19/003* (2013.01)

(58) Field of Classification Search
CPC ................... A61C 13/0024; A61C 13/1016
See application file for complete search history.

(56) References Cited

U.S. PATENT DOCUMENTS

| | | | |
|---|---|---|---|
| 3,813,777 A | 6/1974 | Van Handel et al. | |
| 4,227,877 A | 10/1980 | Tureaud et al. | |
| 4,361,528 A | 11/1982 | Ginsburg et al. | |
| 4,370,133 A | 1/1983 | Stempel | |
| 4,413,979 A | 11/1983 | Ginsburg et al. | |

(Continued)

OTHER PUBLICATIONS

International Search Report for PCT/US14/24579—filed Mar. 12, 2014. ISR mailed Oct. 23, 2014.

(Continued)

*Primary Examiner* — Benjamin Schiffman
(74) *Attorney, Agent, or Firm* — Robert W. Morris; Eckert Seamans Cherin & Mellott, LLC

(57) ABSTRACT

Dental devices and systems and methods for making dental devices are described herein. In some embodiments, denture base material may be adapted to fit a model of a patient's mouth, and a pre-set arch of denture teeth may be adjusted the model. The pre-set arch may be impressed into the denture base material to create a channel. In some embodiments, the cure may be a partial cure and/or a releasing agent may be used such that the pre-set arch may be removed, if needed for further adjustments, after assessing the fit of the denture device. If the fit is correct, another cure may be performed to finish the denture device. If the fit is incorrect, a new bite registration and/or adjustments to the denture base material and/or pre-set arch of denture teeth may be made.

20 Claims, 14 Drawing Sheets

(56) References Cited

U.S. PATENT DOCUMENTS

| | | | |
|---|---|---|---|
| 4,654,006 | A | 3/1987 | Kusano et al. |
| 4,808,184 | A | 2/1989 | Tepic |
| 5,304,063 | A | 4/1994 | Ginsburg |
| 5,403,186 | A | 4/1995 | Ginsburg |
| 5,775,900 | A | 7/1998 | Ginsburg et al. |
| 2007/0190488 | A1 | 8/2007 | Rusler |
| 2008/0108007 | A1 | 5/2008 | Kong et al. |
| 2010/0196856 | A1* | 8/2010 | Mancino ............ A61C 13/0003 433/201.1 |
| 2010/0283168 | A1* | 11/2010 | Vandor .................. A61C 13/34 264/17 |
| 2010/0297581 | A1 | 11/2010 | Wallace |
| 2011/0129796 | A1* | 6/2011 | Riggio ................. A61C 9/0006 433/171 |
| 2012/0107771 | A1 | 5/2012 | Hrenak |
| 2013/0218532 | A1* | 8/2013 | Thompson ......... A61C 13/0004 703/1 |
| 2014/0272787 | A1 | 9/2014 | Ginsburg et al. |
| 2015/0238292 | A1* | 8/2015 | Boe .................... A61C 13/0025 433/171 |
| 2016/0367344 | A1* | 12/2016 | Heffelfinger ......... A61C 13/097 |

OTHER PUBLICATIONS

Dentistry Today, Ginsberg, Stephen J. and Cavalier, Neil. A New Two-Appointment Custom Denture Technique. [online], Aug. 31, 2002, pp. 1-5, [retrieved on Jul. 31, 2014], retrieved from the Internet: http://www.dentistrytoday.com/prosthodontics/prosthetics/1729.

Glidewell Laboratories, Inclusive Screw-Retained Hybrid Denture [online], http://www.glidewelldental.com/lab/services/inclusive-screw-retained-denture.aspx, 2011, pp. 1 and 2, [retrieved on Jul. 31, 2014], retrieved from the Internet: http://web.archive.org/web/20111001035339/http://www.glidewelldental.com/lab/services/inclusive-screw-retained-denture.aspx.

Pritidenta, priti® process [online], http://www.pritidenta.com/cms/pritiprocess.html, 2013, pp. 1 and 2 [retrieved on Jul. 31, 2014], retrieved from the Internet: http://web.archive.org/web/20130225183443/http://www.pritidenta.com/cms/pritiprocess.html.

Miradent.com, Dental Thermoplastics for the Future [online], http://www.miradent.com/index.shtml, 2002, [retrieved on Jul. 31, 2014], retrieved from the Internet: http://web.archive.org/web/20020628124333/http://www.miradent.com/index.shtml.

Miradent.com, Miradent Products [online], http://www.miradent.com/products/, 2002, [retrieved on Jul. 31, 2014], retrieved from the Internet: http://web.archive.org/web/20020628125147/http://www.miradent.com/products/.

Miradent.com, The 1 Visit Miradent Denture (Product Instructions) [online], http://miradent.com/products/productinstructions196.shtml, 2002, pp. 1-5, [retrieved on Jul. 31, 2014], retrieved from the Internet: http://web.archive.org/web/20020628125259/http://www.miradent.com/products/productinstructions196.shtml.

Miradent.com, The 1 Visit Miradent Denture (Product Overview) [online], http://www.miradent.com/products/productoverview196.shtml, 2002, [retrieved on Jul. 31, 2014], retrieved from the Internet: http://web.archive.org/web/20020706084827/http://www.miradent.com/products/productoverview196.shtml.

Miradent.com, The C&B Tray (Product Instructions) [online], http://www.miradent.com/products/productinstructions197.shtml, 2002, pp. 1-3, [retrieved on Jul. 31, 2014], retrieved from the Internet: http://web.archive.org/web/20020714050500/http://www.miradent.com/products/productinstructions197.shtml (captured ).

Miradent.com, The C&B Tray (Product Overview) [online], http://www.miradent.com/products/productoverview197.shtml, 2002, [retrieved on Jul. 31, 2014], retrieved from the Internet: http://web.archive.org/web/20021007223937/http://www.miradent.com/products/productoverview197.shtml (captured ).

Miradent.com, The Denture Arch (Product Instructions) [online], http://www.miradent.com/products/productinstructions231.shtml, 2002, pp. 1 and 2, [retrieved on Jul. 31, 2014], retrieved from the Internet: http://web.archive.org/web/20020628125332/http://www.miradent.com/products/productinstructions231.shtml (captured ).

Miradent.com, The Denture Arch (Product Overview) [online], http://www.miradent.com/products/productoverview231.shtml, 2002, [retrieved on Jul. 31, 2014], retrieved from the Internet: http://web.archive.org/web/20021007230707/http://www.miradent.com/products/productoverview231.shtml.

Miradent.com, The Denture Tray (Product Instructions) [online], http://www.miradent.com/products/productinstructions200.shtml, 2002, pp. 1-3, [retrieved on Jul. 31, 2014], retrieved from the Internet: http://web.archive.org/web/20020628125251/http://www.miradent.com/products/productinstructions200.shtml.

Miradent.com, The Denture Tray (Product Overview) [online], http://www.miradent.com/products/productoverview200.shtml, 2002, [retrieved on Jul. 31, 2014], retrieved from the Internet: http://web.archive.org/web/20020628130431/http://www.miradent.com/products/productoverview200.shtml.

Miradent.com, The Emergency Denture (Product Instructions) [online], http://www.miradent.com/products/productinstructions232.shtml, 2002, [retrieved on Jul. 31, 2014], retrieved from the Internet: http://web.archive.org/web/20021020140119/http://www.miradent.com/products.productinstructions232.shtml.

Miradent.com, The Emergency Denture (Product Overview) [online], http://www.miradent.com/products/productoverview232.shtml, 2002, [retrieved on Jul. 31, 2014], retrieved from the Internet: http://web.archive.org/web/20021212053820/http://www.miradent.com/products/productoverview232.shtml.

Miradent.com, The Implant Insta Stent & Surgical Guide (Product Instructions) [online], http://www.miradent.com/products/productinstructions198.shtml, 2002, pp. 1-3, [retrieved on Jul. 31, 2014], retrieved from the Internet: http://web.archive.org/web/20020628125257/http://www.miradent.com/products/productinstructions198.shtml.

Miradent.com, The Implant Insta Stent & Surgical Guide Overview [online], http://www.miradent.com/products/productoverview198.shtml, 2002, [retrieved on Jul. 31, 2014], retrieved from the Internet: http://web.archive.org/web/20020628130304/http://www.miradent.com/products/productoverview198.shtml.

Miradent.com, The Interim Denture (Product Instructions) [online], http://www.miradent.com/products/productinstructions199.shtml, 2002, [retrieved on Jul. 31, 2014], retrieved from the Internet: http://web.archive.org/web/20020628125218/http://www.miradent.com/products/productinstructions199.shtml.

Miradent.com, The Interim Denture (Product Overview) [online], http://www.miradent.com/products/productoverview199.shtml, 2002, [retrieved on Jul. 31, 2014], retrieved from the Internet: http://web.archive.org/web/2002062813052/http://www.miradent.com/products/productoverview199.shtml.

Miradent.com, The Vanity Denture (Product Instructions) [online], http://www.miradent.com/products/productinstructions201.shtml, 2002, [retrieved on Jul. 31, 2014], retrieved from the Internet: http://web.archive.org/web/20021221133938/http://www.miradent.com/products/productinstructions201.shtml.

Miradent.com, The Vanity Denture (Product Overview) [online], http://www.miradent.com/products/productoverview201.shtml, 2002, [retrieved on Jul. 31, 2014], retrieved from the Internet: http://web.archive.org/web/20021007224513/http://www.miradent.com/products/productoverview201.shtml.

Miradent.com, Miradent Technology [online], http://www.miradent.com/technology/, 2002, [retrieved on Jul. 31, 2014], retrieved from the Internet: http://web.archive.org/web/20020628130607/http://www.miradent.com/technology/.

Miradent.com, The Denture Form—How It Works [online], http://miradent.com/products-dentureform.shtml, 2007, pp. 1-3 [retrieved on Jul. 31, 2014], retrieved from the Internet: http://web.archive.org/web/20070430170333/http://miradent.com/products-dentureform.shtml (captured ).

AvaDent, Products [online], pp. 1-7, [retrieved on Jul. 31, 2014], retrieved from the Internet: http://web.archive.org/web/20130608184533/http://www.avadent.com/professional/solutions/.

(56) References Cited

OTHER PUBLICATIONS

AvaDent, Getting Started with AvaDent Kit [online], prior to Mar. 6, 2013, pp. 1-3, [retrieved on Jul. 31, 2014], retrieved from the Internet: https://store.avadent.com/Getting-started-with-AvaDent-kit.html.

AvaDent, Computer precision fit [online], 2013, pp. 1-3, [retrieved on Jul. 31, 2014], retrieved from the Internet: http://web.archive.org/web/20130608184533/http://www.avadent.com/professional/solutions/.

Dentca.com, http://dentca.com/, 2012, pp. 1 and 2 [retrieved on Jul. 31, 2014], retrieved from the Internet: http://web.archive.org/web/20120225051951/http://dentca.com/.

Dentca.com, About DENTCA [online], http://www.dentca.com/aboutUs.asp, 2012, pp. 1 and 2, [retrieved on Jul. 31, 2014], retrieved from the Internet: http://web.archive.org/web/20120618144630/http://www.dentca.com/aboutUs.asp.

Envisiontec.de, the benchmark in 3D printing [online], http://www.envisiontec.de/, 2013, pp. 1 and 2, [retrieved on Jul. 31, 2014], retrieved from the Internet: http://web.archive.org/web/20130306062409/http://www.envisiontec.de/ (captured Mar. 6, 2013).

Envisiontec.com, Dental [online], http://envisiontec.com/applications/dental/, 2013, pp. 1 and 2, [retrieved on Jul. 31, 2014], retrieved from the Internet: http://web.archive.org/web/20130316071646/http://envisiontec.com/applications/dental/.

Envisiontec, Octoflash [online], Dec. 2012, [retrieved on Jul. 31, 2014], retrieved from Internet: http://envisiontec.com/envisiontec/wp-content/uploads/2012/12/Machine-Otoflash.pdf.

Envisiontec, PixCera [online], Dec. 2012, [retrieved on Jul. 31, 2014], retrieved from Internet: http://envisiontec.com/envisiontec/wp-content/uploads/2012/12/Machine-PixCera.pdf.

Envisiontec, 3DENT [online], Dec. 2012, [retrieved on Jul. 31, 2014], retrieved from Internet: http://envisiontec.com/envisiontec/wp-content/uploads/2013/02/MK-MCS-3Dent-V01-FN-EN.pdf.

Envisiontec, Brochure [online], Dec. 2012, [retrieved on Jul. 31, 2014], retrieved from Internet: http://envisiontec.com/envisiontec/wp-content/uploads/2012/12/MK-NOA-DentalBrochure-V01-FNf-EN.pdf.

\* cited by examiner

METHOD OF FABRICATING A DENTURE

CROSS-REFERENCE TO RELATED APPLICATIONS

This application claims the benefit of U.S. Provisional Patent Application No. 61/996,679, which was filed on May 14, 2014, the disclosure of which is incorporated herein by reference in its entirety.

FIELD OF INVENTION

This application generally relates to dental devices, such as dentures, and systems and methods for making the same.

BACKGROUND

The unnatural loss of one's teeth is one of the biggest health issues in the world today. Aside from normal teeth loss that commonly occurs from childhood to early adulthood, loss of one's teeth due to old age and/or poor oral hygiene care affects millions of people worldwide. Furthermore, as people continue to live longer and longer, this condition will continue resulting in more and more individuals relying on dentures to replace some or all of their teeth.

Dentures, however, can be embarrassing for some people to wear. Individuals may believe, for example, that dentures look and feel unnatural. Many elderly people, however, rely on dentures to assist them in a large number of their daily activities. For instance, not only can dentures provide one with the ability to chew and enjoy a good meal, they can also help people speak properly, as well as put on a confident smile. Thus, dentures are critical for helping people suffering from unnatural teeth loss to stay nourished as well as improve their mental state.

Although dentures provide many advantages to a patient, the patient may be required to visit their dental practitioner (e.g., a prosthodontist) multiple times to obtain a properly fitting set of dentures. Additionally, the dental practitioner may also have to rely upon an equal number of laboratory procedures to obtain a suitable set of dentures for a patient, such that the dentures have the right look, feel, and fit. For example, a practitioner may have to individually set teeth in wax forms based on data provided by a dentist. This process, however, may be time consuming and labor intensive for the practitioner. Furthermore, at each dental visit, the practitioner may test the fit and feel of the denture device. If there are modifications needed to be made to the denture device, the practitioner may have to send an interim denture back to a denture manufacturer to perform any adjustments needed to be made, which further exacerbates the cost and time associated with obtaining properly fitting dentures as these adjustments require the manual labor of highly skilled technicians.

In light of the aforementioned, denture fabrication may appear part art and part science. For instance, a particular adjustment to a denture, performed by a given technician on a given day, may be different than the same adjustment made by the same technician on a different day. Any slight error in the placement of one or more teeth in a denture (e.g., a lower or mandibular denture) may render it incompatible with a counterpart denture (e.g., an upper or maxillary denture). This error-prone and inefficient process of fine tuning a denture increases dental costs, and can frustrate both the practitioner and the patient. Conventional denture fabrication thus involves a series of time consuming and expensive laboratory procedures and so there is a need for improved dental devices and systems and methods for the same.

Thus, it would be beneficial for there to be improved dental devices, and systems and methods for making the same, that enable a dental device to be created efficiently such that a patient may obtain a properly fitting denture without excess cost and time expenditure.

SUMMARY OF THE INVENTION

The present disclosure generally relates to dental devices, such as dentures, and systems and methods for making the same that improve upon the known difficulties mentioned above.

In one exemplary embodiment, a method for fabricating a denture is described. An amount of uncured denture base material may be adapted to a model of a patient's mouth. For example, a bite registration or impression of a patient's mouth may be obtained, and denture base material may be adapted to the model formed from the bite registration or impression. A pre-set arch of teeth, either partial or full, may then be adjusted to fit the model of the patient's mouth. For example, the pre-set arch of teeth may be heated in boiling water (e.g., 100-degrees Celsius), which may allow the pre-set arch of teeth to become moldable and capable of being adjusted along an arch width and/or occlusal planes of the pre-set arch of denture teeth. After the pre-set arch of denture teeth is adjusted, a bonding agent may be applied to a denture base portion of the pre-set arch of denture teeth that will contact the uncured denture base material. The pre-set arch of teeth may then be impressed into an occlusal surface of the uncured denture base material, causing a channel to be created within the uncured denture base material. The uncured denture base material with the pre-set arch of denture teeth impressed therein may then be cured, for instance using an ultraviolet ("UV") light source, to form a substantially unitary denture device.

In another exemplary embodiment, an arch device for a denture is described. The arch device may include a denture base made of a denture base material, a channel formed along an occlusal surface of the denture base, and a pre-set arch of denture teeth. The pre-set arch of denture teeth may also have an amount of the denture base material applied to at least one of a buccal portion, a labial portion, and a lingual portion of the pre-set arch of denture teeth.

In yet another exemplary embodiment, another method for fabricating a denture is described. An amount of uncured denture base material may be adapted to a model a patient's mouth, and a pre-set arch of denture teeth may be adjusted to fit the model of the patient's mouth. In some embodiments, a releasing agent may be applied to a denture base portion of the pre-set arch of denture teeth. The pre-set arch of denture teeth may then be impressed to an occlusal surface of the uncured denture base material to create a channel within the uncured denture base material. A first cure of the uncured denture base material and the pre-set arch of denture teeth may then be performed that causes the uncured denture base material to become partially cured. For example, a partial cure or a full cure may be performed on the uncured denture base material. After the first cure, a test of a first cured denture device formed of the first cured denture base material and the pre-set arch of denture teeth may be performed to determine if the first cured denture device is formed correct. If the first cured denture device has been formed correctly, the pre-set arch of denture teeth may be removed from the first cured denture base material, and a bonding agent may be applied to the denture base portion of the pre-set arch of denture teeth. For example, the bonding agent may be applied in a similar location and fashion as the releasing agent. After the bonding agent has been applied, the pre-set arch of denture teeth may be pressed into the channel of the first cured denture base material. A second cure may then be performed to the first cured denture base material with the pre-set arch of denture teeth pressed therein to form a substantially unitary denture device.

BRIEF DESCRIPTION OF THE DRAWINGS

The above and other features of the present invention, its nature and various advantages will be more apparent upon consideration of the following detailed description, taken in conjunction with the accompanying drawings in which.

DESCRIPTION OF EMBODIMENTS

Figure 1:
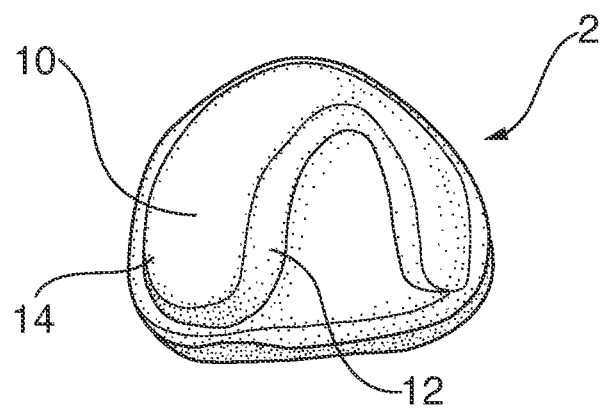
FIG. 1 is an illustrative diagram of a model of a patient's mouth in accordance with various embodiments.

Arches, or denture arches (e.g., pre-set arches of denture teeth set in an adjustable denture base material), such as those described herein, can simplify or eliminate a number of the conventional steps for fabricating a denture (e.g., individual tooth setting, festooning, and detailed trimming & polishing of the final denture). Moreover, additional systems and methods (also described herein) extend those advantages to simplify or eliminate additional steps in the conventional denture fabrication process, resulting in a significant reduction in overall laboratory time and costs commonly associated with creating and obtaining denture devices.

Generally speaking, it is an objective of the present disclosure to make it easier and more efficient for dental practitioners, patients, and dental device laboratories to form one or more suitable dental devices (e.g., dentures) for a patient in as few as a single patient visit. By minimizing the number of times a patient has to visit their dental practitioner, the processes of obtaining a denture may become much more economical and efficient than conventional denture procedures and techniques. Moreover, it is another objective of the present disclosure to fabricate dentures in a more consistent manner over time, such that an otherwise "identical" set of dentures produced at one point in time are substantially similar to another set of "identical" dentures produced at a later point in time.

In at least one embodiment, a dental arch device is provided. The arch device can be similar to an upper denture, and can correspond and fit to an upper portion of a patient's mouth, such as an upper or maxillary jaw. Alternatively, the arch device can be similar to a lower denture, and can correspond and fit to a lower portion of a patient's mouth, such as a lower or mandibular jaw. For example, an arch device can be constructed to fit to a corresponding one of a patient's upper (or maxillary) and lower (or mandibular) teeth and gum portions. The arch device can serve as at least a partial replacement for one or more teeth of that portion. The arch device may be composed of one or more materials or compounds that are compatible with a patient's mouth. More particularly, the compounds can be chemically compatible with the inside of a patient's mouth. For example, the compounds can include polymethyl methacrylate ("PMMA") thermoplastic.

The arch device can be smaller than a full or conventional denture. A typical denture includes a set of teeth coupled to a uniform base material. The uniform base material includes a lingual section (e.g., the curved teeth retaining portion of the denture facing a tongue or oral cavity) coupled to the teeth, and a framework or flange section that provides overall structural integrity to the denture and that extends from the lingual section to a border of the denture. When the arch device is used to fabricate a denture, base material can be added to the base of the arch device to form a flange for the resulting denture. In this manner, the arch device can constitute a lingual portion of the denture that is integrated to a distinct flange portion.

The arch device can be employed during a patient's fitting session. For example, the arch device can be inserted and coupled to a corresponding portion of the patient's mouth. It can often be the case, however, that even when an arch device is suitably sized for a patient, the arch device may not fit precisely or comfortably in the patient's mouth. Thus, in at least one embodiment, the arch device can be adjustable. More particularly, the arch device can be constructed from one or more materials that allow the arch device to be pliable or flexible. The arch device may not always be adjustable, however. Rather, the arch device may only be adjustable when subjected to certain temperatures. For example, the arch device may only be adjustable when heated above certain temperatures (e.g., greater than, or equal to 100-degrees Celsius). Thus, during a patient visit, if a particular arch device selected by a dental practitioner appears to be insertable into the patient's mouth, but may need certain minor adjustments, there would be no need to send the arch device to a dental device manufacture for any adjustments. Rather, the practitioner can simply heat the arch device to at least a predefined temperature, and can make the necessary adjustments to the arch device on the spot. For example, the arch device can be subjected to heat for a few minutes, and then it can be adjusted to the shape needed for a comfortable fit, and then can be re-inserted into the patient's mouth to check the fit. This adjustment process can be repeated until the arch device fits properly and comfortably in the patient's mouth.

Each arch device can be processed to form a complete set of dentures for the patient. For example, a base material (e.g., wax or acrylic portion) can be added to each arch device to form a complete denture that includes a lingual portion and a distinct flange portion. This step can be performed either directly by a dental practitioner during a patient visit, or by a laboratory technician. If it is performed by the latter, the patient can be required to make at least another visit after the laboratory procedure.

Some patients may have existing teeth, but may require a "flipper" device or a bridge to substitute for one or more missing teeth. Thus, in at least one embodiment, an arch device can be similarly modified to form a partial arch device. In these embodiments, select portions of a complete arch device can be trimmed or cut to form one or more grooves for receiving a patient's existing teeth. The modified arch device can then only include teeth that correspond to the patient's missing teeth. As with a complete arch device, the modified arch device can also be adjusted (e.g., as described above) to fit in the patient's mouth and function as an instant flipper or bridge. Any cut portions of the modified arch device can also be cold cured (e.g., with acrylic) to smoothen any sharp edges or surfaces. In at least one embodiment, when the modified arch device is used to provide a bridge for a patient, one or more implants or abutments can be prepared, and the corresponding teeth of the modified arch device can be fitted to the implants or abutments.

An arch device (partial or full) can be fabricated using any suitable methods. These methods can include, for example, computer-aided design ("CAD"), computer-aided manufacturing ("CAM"), three-dimensional (3-D) printing, and the like. Moreover, dentures can be fabricated by leveraging an arch device, in conjunction with one or more of computer-aided design ("CAD"), computer-aided manufacturing ("CAM"), three-dimensional (3-D) printing, and the like.

Computer-aided design ("CAD") and computer-aided manufacturing ("CAM") systems can deliver products rapidly and with unprecedented accuracy of fit. These systems have been successfully employed to fabricate various dental products. For example, CAM production or CAM-milling techniques have been successfully used to fabricate reliable crowns. However, conventional CAD and CAM techniques have failed to efficiently and reliably fabricate dentures. One of the biggest challenges with CAM of dentures has to do with poor fitting of teeth in CAM-milled denture bases. As briefly described above, dentures are chiefly composed of at least two distinct materials—a pink acrylic for the base (e.g., gingiva) and flange portion and a white acrylic (or porcelain) for the teeth. Some dentures can include three or more different materials, depending on a number of layers that make up the teeth. For example, some teeth can be made of at least two layers of acrylic of slightly different colors, and sometimes even three or more layers). Because typical CAM milling "work" blocks of uniform material, the fabricated teeth are limited to single-layer teeth, which can be inferior to two- or higher-layer teeth (e.g., in structural integrity, look, and feel). Consequently, the current state-of-the art in CAM milling of dentures involves milling the gingiva portion, and then gluing third-party manufactured teeth to the CAM-milled gingiva.

However, while CAM-milled gingiva holes (e.g., for receiving or coupling to the teeth) can be fabricated with tolerances on the order of about 10 microns, the dimensions of third-party manufactured teeth can have much larger variations or tolerances, especially due to any polishing and finishing processes that occur after the teeth are pressed. This can make it difficult to accurately fit the teeth in corresponding CAM-milled gingiva holes. Moreover, even if CAM-milled denture teeth can be fabricated to aesthetically compete with multi-layer conventionally fabricated teeth, the milled teeth may still require polishing or processing after milling, which may create similar dimensional variations.

Additionally, to fabricate dental devices using CAD and CAM techniques, it is necessary to obtain a model of a patient's mouth, and to create a design of a denture based on the model. However, conventional techniques of creating a physical model of a patient's mouth can include various steps, such as taking multiple impressions, fabricating models and a custom impression tray, creating a master cast, and determining jaw and occlusal relationships. Because these steps can require multiple patient visits, conventional modeling techniques are unable to leverage the speed and economics of CAD and CAM denture fabrication.

Thus, in various embodiments, the efficiencies of CAD and CAM techniques are leveraged to fabricate dental devices, dentures, and the like, while overcoming one or more of the above-described shortcomings.

In at least one embodiment, a denture form device can be employed to obtain a physical model of a patient's mouth during a CAD and CAM denture fabrication process. More particularly, when a denture form device is inserted and adjusted to fit to a corresponding portion of a patient's mouth, the adjusted denture form device can serve as a physical model of the portion of the patient's mouth, and can provide data including, but not limited to, final impressions anatomy, anatomic landmarks and extensions, vertical dimension, midline, centric relation, smile line, incisal length, interpupillary and ala tragus planes, tooth size, shade, and mold. This model can be provided to a CAD system (e.g., by scanning using a 3-D scanner or the like) for generating a denture model of a corresponding denture. This denture model can then be provided to a CAM system for fabricating an actual denture.

In at least one embodiment, a physical model of a patient's mouth can additionally, or alternatively, be obtained via an intra-oral scan of the mouth. For example, the scan can obtain information on intra-oral cavity, remaining teeth (if any), implants (if any), soft tissue, skeletal devices (e.g., from CT scans), external facial features across a range of facial gestures, jaw movement, and the like. The scanned data can be integrated using software to create a digital model of the patient's mouth that is suitable for creating a denture design that has proper fit, alignment, and occlusion.

In at least one embodiment, an arch device (such as that described above) can be combined with CAD and CAM techniques to fabricate a denture. For example, a physical model of a patient's mouth (e.g., obtained by using a denture form device or by intra-oral scan of the patient's mouth) can be provided to a system (e.g., a computer system) that has access to a database of digital models (e.g., pre-scanned and pre-stored models) of multiple arch devices.

The system can select an arch device that matches the physical model. For example, the system can select the arch device based on the size of the arch device and the size of the teeth of the arch device. As another example, the system can select the arch device based on tooth shade, photographs of patient's existing teeth, and the like. As yet another example, the system can select the arch device based on general patient information, such as gender, patient preferences, clinician or practitioner preferences, and the like.

In instances where none of the available arch device models is a close match with the physical model, each arch device model can be augmented with a tolerance range (e.g., either by manual input or via one or more digital scans of the corresponding actual arch devices). This additional data for each arch device model can provide information on an amount of adjustment (e.g., in any dimension) that can be made to each arch device, while maintaining the structural and aesthetic integrity of each arch device. In this manner, the system can identify an arch device that most closely matches the physical model. Moreover, the system can also provide adjustment information on how (e.g., in what dimensions and to what degree) the arch device should be adjusted to achieve a proper fit. A dental practitioner (e.g., a clinician) can then select the actual arch device corresponding to the chosen arch device model, and can adjust the arch device based on the adjustment information. In at least one embodiment, the system can also obtain a digital scan of the adjusted arch device to create an adjusted arch device model. The system can further determine if the adjusted arch device will provide a good fit based on the adjusted model. The above process can be repeated until a suitable arch device, with the proper adjustments, is identified.

This model can be provided to a CAD system (e.g., by scanning using a 3-D scanner or the like) for generating a denture model of a corresponding denture. This denture model can then be provided to a CAM system for fabricating an actual denture. After an appropriate arch device is selected and adjusted, a digital model of a CAM-fabricated denture base (e.g., via milling or 3-D printing) can be manipulated in size and orientation (e.g., a channel can be formed in the digital model of the denture base) so as to guide an integration of the arch device to the CAM-fabricated denture base. This can ensure that proper occlusion in the digital model of the denture base is maintained in a final denture.

Since an arch device already includes teeth, it may not be necessary to CAM a gingiva base portion that includes holes for receiving teeth. This can eliminate the above-described problem of teeth variations or tolerances. Rather, a CAM-milled denture base may only be required to include a relatively tolerant surface (e.g., on the order of millimeters, and not microns) for integrating to a base of the arch device, which can be fabricated within any tolerance ranges.

FIG. 1 is an illustrative diagram of a model of a patient's mouth in accordance with various embodiments. Model 2 of FIG. 1 may, in some embodiments, be obtained by a dental practitioner during a patient visit. Model 2, as described above, may be formed using various scanning techniques harness with CAD systems, or via more conventional techniques, such as impressions and molds. For example, a 3-D scan of a patient's mouth may be obtained using an intra-oral scanner, which may be sent to a 3-D printer to create model 2 of the patient's mouth.

Model 2 may include ridge portion 10 which is substantially arch-shaped. Persons of ordinary skill in the art will recognize that although model 2 corresponds to an upper or maxillary portion of a patient's mouth, this is merely illustrative, and model 2 may include a lower mandibular portion in addition to, or instead of, the upper portion. Ridge 10 corresponds, in some embodiments, to a portion of a patient's teeth and/or gums, such as an upper or lower mandibular portion of a patient's mouth. For example, if model 2 corresponds to a lower mandibular portion of a patient's mouth, ridge 10 would correspond to a shape of the patient's teeth and/or gums as they protrude towards the upper mandibular portion of the patient's mouth.

Model 2 also includes inner portion 12. Inner portion 12 corresponds to a portion of the patient's mouth substantially enclosed (except for a portion near the throat) by a user's teeth. For example, if model 2 corresponds to an upper mandibular portion of a patient's mouth, inner portion 12 may correspond to a palate portion. As another example, if model 2 corresponds to a lower mandibular portion of a patient's mouth, inner portion 12 may correspond to a lingual portion, or portion of the base of the patient's mouth where the patient's tongue is located.

Model 2 further may, in some embodiments, include excess modeling material 14. For example, if an impression is used to obtain a model of the patient's mouth, excess modeling material 14 may represent a portion of the modeling material that extends past the bounds of the impression tray. As another example, excess modeling material 14 may correspond to an inner cheek portion of the patient's mouth. As still yet another example, CAM techniques may form model 2 out of a larger block of material, which, when trimmed away, may leave ridge 10, inner portion 12, and excess portion 14.

Figure 2:
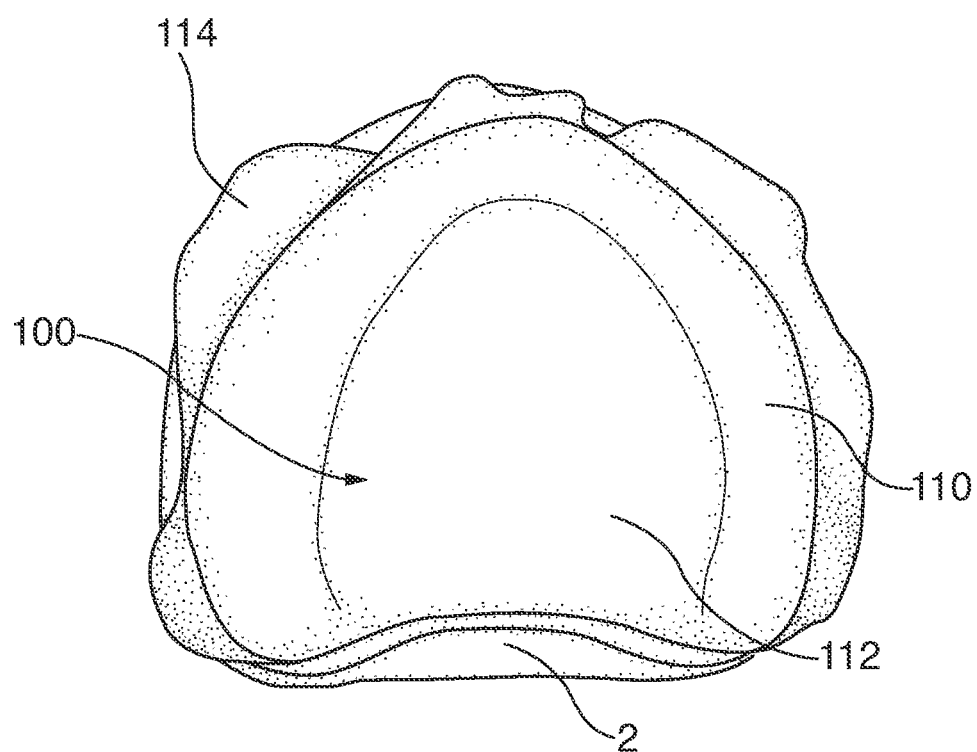
FIG. 2 is an illustrative diagram of an amount of denture base material adapted to the model of the patient's mouth of FIG. 1, in accordance with various embodiments.

FIG. 2 is an illustrative diagram of an amount of denture base material adapted to the model of the patient's mouth of FIG. 1, in accordance with various embodiments. Denture base material 100, in some embodiments, may be adapted to a model of a patient's mouth, such as model 2 of FIG. 1. For example, a dental practitioner or laboratory technician may take an amount of denture base material suitable to substantially cover at least one entire side (e.g., upper side, lower side) of model 2. In some embodiments, the amount of denture base material may be sufficient to substantially cover the entire model, an upper or lower portion of the model, or only a section (e.g., where a missing tooth or teeth may be) of the model.

In some embodiments, denture base material 100 may be a light-cure material that may harden or become rigid in response to being subjected to an amount of light. For example, denture base material 100 may harden when subjected to ultra-violent ("UV") light. As another example, denture base material 100 may harden when subjected to a high-intensity white light. In some embodiments, the light-cure material of denture base material 100 may partially harden in response to being subject to light, such as UV light or a high-intensity white light, for a first amount of time. For example, denture base material 100 may be subjected to high-intensity white light for approximately 2-3 minutes, which may cause denture base material 100 to harden such that it retains its shape but may still be partially malleable. As another example, denture base material 100 may be subjected to UV light for approximately 10 minutes, which may cause denture base material 100 to harden completely such that a solid, non-malleable, structure is formed. In some embodiments, denture base material 100 may be an auto-polymerizing material that hardens when left untouched for a certain amount of time such that the auto-polymerizing material may cure. For example, the auto-polymerizing material may cure through an internal hardening reaction process. In some embodiments, the denture base material may be an acrylic or a urethane acrylate polymer, however persons of ordinary skill in the art will recognize that other materials may be used.

Denture base material 100 of FIG. 2 may include ridge portion 110 and inner portion 112. Ridge portion 110 may correspond to a portion of denture base material 100 that is placed on ridge portion 10 of model 2. Inner portion 112 may correspond to a portion of denture base material 100 that is placed on inner portion 12 of model 2. Similarly, excess denture base material 114 may correspond to any portion of denture base material 100 that is placed on excess portion 14 of model 2, or any excess amount of denture base material 100.

Denture base material 100 may be placed on model 2 such that denture base material 100 substantially fits model 2. For example, denture base material 100, when adapted to model 2, may not include any air pockets or missing portions. This may allow a substantially consistent and uniform denture to be formed from denture base material 100.

Figure 3A:
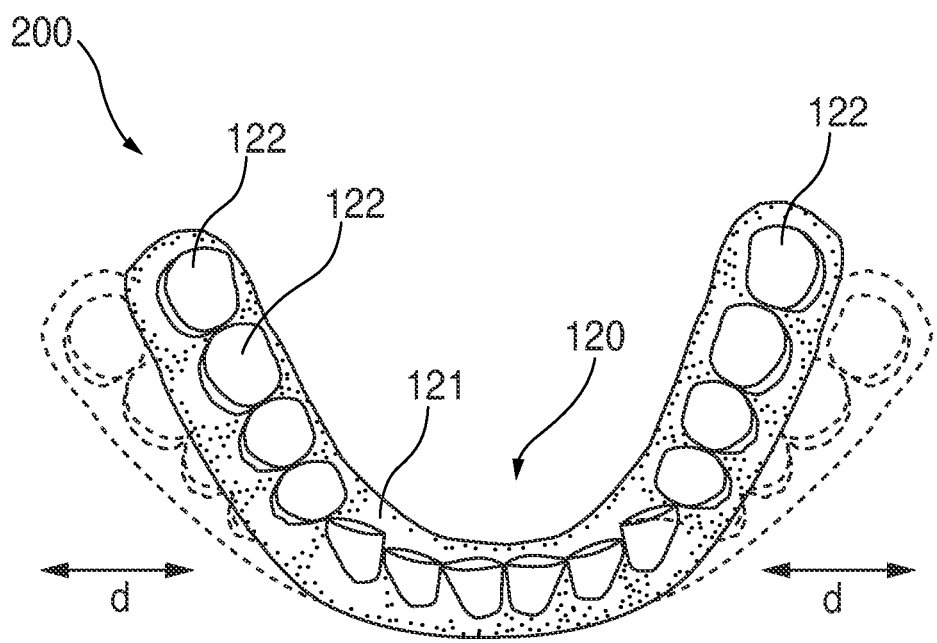
FIGS. 3A and 3B are illustrative diagrams of a front perspective view and a side view, respectively, of a pre-set arch of denture teeth in accordance with various embodiments.
Figure 3B:
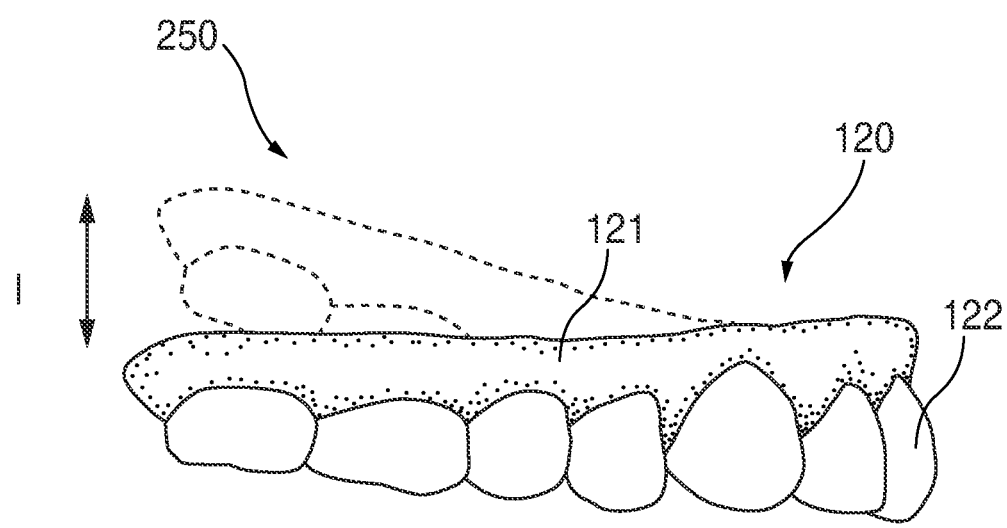

FIGS. 3A and 3B are illustrative diagrams of a front perspective view and a side view, respectively, of a pre-set arch of denture teeth in accordance with various embodiments. Front perspective view 200 and side view 250 may each include pre-set arch 120 of denture teeth. The pre-set arch of denture teeth may, in some embodiments, include one or more denture teeth 122 (e.g., artificial teeth), coupled to a uniform base material 121. Uniform base material 121 of pre-set arch 120 of denture teeth 122 may, in some embodiments, include a lingual section (e.g., the curved teeth retaining portion of a denture facing a tongue or an oral cavity) coupled to denture teeth 122, and a framework or flange section that provides overall structural integrity to the denture, when formed, and that extends from the lingual section to a border of the denture.

In some embodiments, pre-set arch 120 may include a full set of denture teeth 122 for either an upper or lower portion of a patient's mouth. However, in other embodiments, pre-set arch 120 may include a portion of the full set of denture teeth 122 corresponding to sections of a patient's mouth where one or more teeth may be missing.

In some embodiments, pre-set arch 120 may be moldable or capable of being molded, shaped, or adjusted. In response to being subjected a certain amount of heat for a certain amount of time, uniform base material 121 of pre-set arch 120 may become malleable such that pre-set arch 120 may be adjusted. For example, pre-set arch 120 may be placed in a container or vat of boiling water (e.g., water have a temperature of 100-degrees Celsius or higher) for several minutes (e.g., 3-5 minutes). As another example, pre-set arch 120 may be placed in an oven or other heating device including, but not limited to, a hot plate, a microwave, or any other apparatus capable of subjecting pre-set arch 120 to heat.

After removing pre-set arch 120 from being subjected to a heating source, a dental practitioner or dental laboratory technician may adjust an arch width and/or an occlusal plane or planes of pre-set arch 120 of denture teeth 122 and/or an amount of base material 121 of pre-set arch 120 such that pre-set arch 120 may fit model 2 of the patient's mouth. For example, an arch width of pre-set arch 120 may be adjusted by an amount d as seen in front perspective view 200. In some embodiments, the arch width may be adjusted such that the amount d extends outwards or inwards, or varies on either side of pre-set arch 120. For example, one occlusal side of pre-set arch 120 may be adjusted in a first direction (e.g., inwards, outwards), while the other occlusal side of pre-set arch 120 may be adjusted in a second direction. In some embodiments, the first direction may extend towards a midline of pre-set arch 120 while a second direction may extend away from midline.

Furthermore, an occlusal plane (on either side) of pre-set arch 120 may be adjusted by an amount l as seen in side view 250. For example, either occlusal portion of pre-set arch 120 may be adjusted such that the occlusal portion is adjusted upwards (e.g., towards an upper portion of a patient's mouth) or downwards (e.g., towards a lower portion of a patient's mouth). The amount l that pre-set arch 120 is adjusted for either occlusal portion may differ or may be similar such that one occlusal portion is adjusted by a first amount and the other occlusal portion is adjusted a second amount. Either occlusal portion of pre-set arch 120 may also be adjusted such that the posterior teeth are rotated outwards (e.g. toward the cheek or lips) or inwards (e.g. toward the tongue). In some embodiments, the adjustments along the arch width and/or occlusal planes may be made to accommodate existing dentition on an opposing arch or on an opposing portion of a patient's mouth. Persons of ordinary skill in the art will recognize that any amount of adjustment may be performed to pre-set arch 120 in any suitable direction, and the aforementioned amount and directions are merely exemplary.

Figure 4:
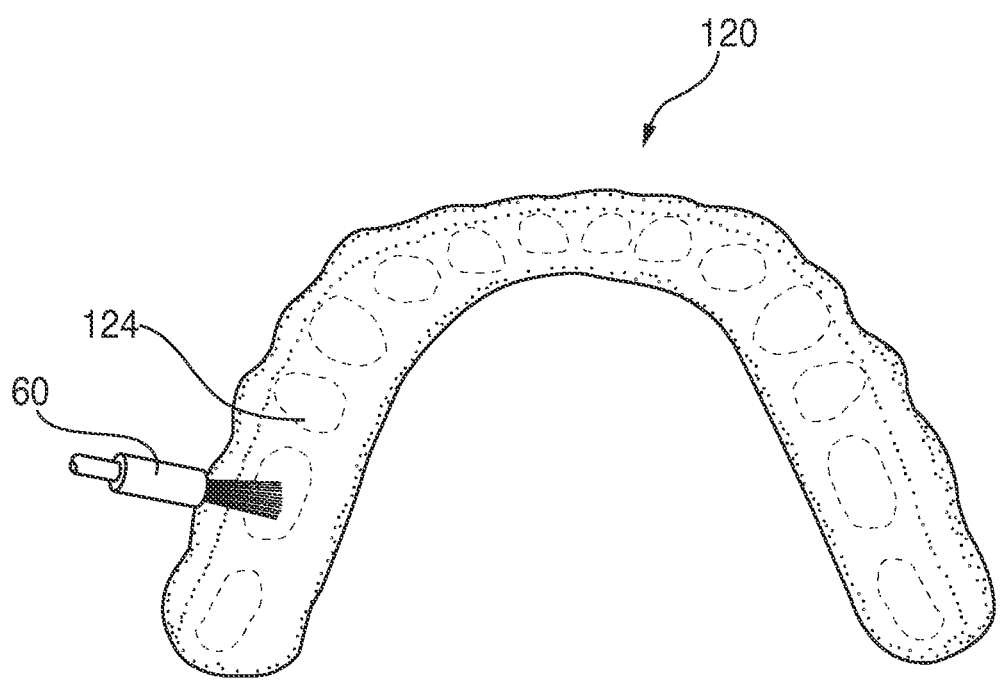
FIG. 4 is a top perspective view of a pre-set arch of denture teeth having an agent applied to a base denture portion in accordance with various embodiments.

FIG. 4 is a top perspective view of a pre-set arch of denture teeth having an agent applied to a base denture portion in accordance with various embodiments. In some embodiments, pre-set arch 120 may have a bonding agent applied to a denture base portion 124 of pre-set arch 120. The bonding agent may be applied to denture base portion 124 using brush 60 or may be applied directly from a container holding the bonding agent (e.g., a tube or container). Denture base portion 124 may, for example correspond to a portion of pre-set arch 120 that will contact denture base material 100, and is located on an opposite side of pre-set arch 120 as compared to one or more denture teeth 122.

In some embodiments, the bonding agent applied by brush 60 to denture base portion 124 may be methyl methacrylate monomer, however any other bonding material or composition may be used. Persons of ordinary skill in the art will further recognize that different denture base materials may use different types of bonding agents, and thus any suitable bonding agent may be used and the aforementioned is merely exemplary. The bonding agent may serve to prepare pre-set arch 120 to be bonded to denture base material 100 that has been adapted to model 2 of the patient's mouth. In some embodiments, in addition to, or instead of, applying the bonding agent to denture base portion 124 of pre-set arch 120, the bonding agent may be applied to a corresponding portion of denture base material 100. For example, the bonding agent may also be applied to ridge 110 of denture base material 100. In yet other embodiments, no bonding agent may be applied, and denture base portion 124 of pre-set arch 120 may have a bonding coated thereon such that, when heated or applied to denture base material 100, pre-set arch 120 may adhere to denture base material 100.

In some embodiment, however, instead of applying a bonding agent to denture base portion 124 to bond pre-set arch 120 to denture base material 100, a releasing agent may be applied to denture base portion 124. For example, a petroleum jelly or petroleum base substance may be applied to denture base portion 124 using brush 60. The releasing agent may, as described in greater detail below, may allow pre-set arch 120 to be easily removed from denture base material 100 after pre-set arch 120 has been impressed into denture base material 100.

Figure 5A:
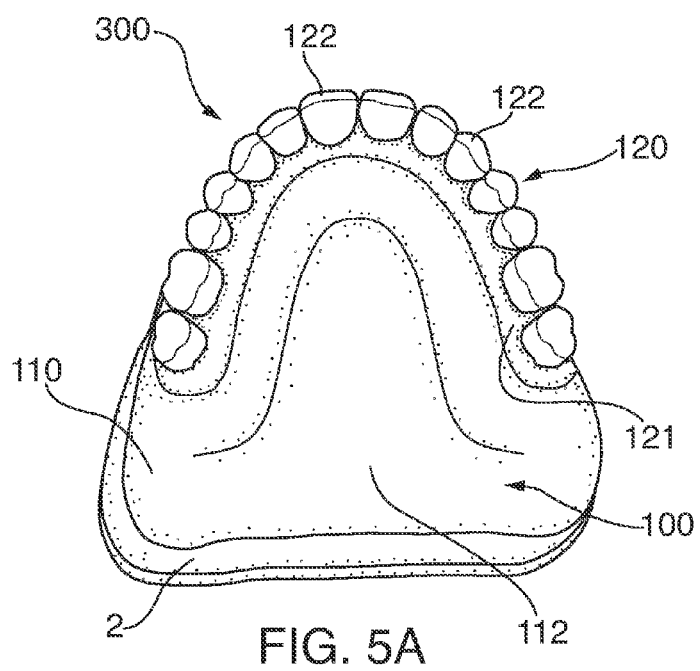
FIGS. 5A and 5B are illustrative diagrams of a pre-set arch of denture teeth positioned and aligned about a ridge of an adapted amount of denture base material and the pre-set arch of denture teeth impressed into the adapted amount of denture base material, respectively, in accordance with various embodiments.
Figure 5B:
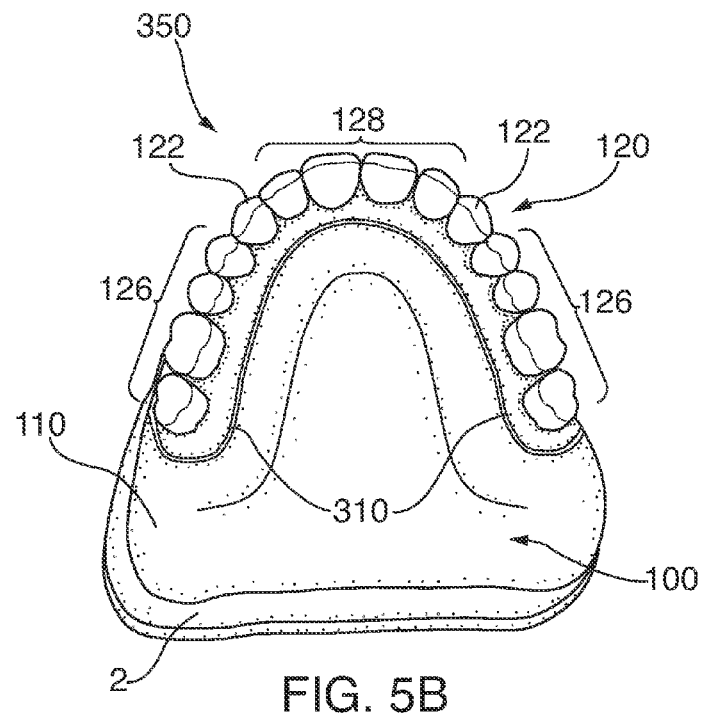

FIGS. 5A and 5B are illustrative diagrams of a pre-set arch of denture teeth positioned and aligned about a ridge of an adapted amount of denture base material and the pre-set arch of denture teeth impressed into the adapted amount of denture base material, respectively, in accordance with various embodiments. System 300 of FIG. 5A includes pre-set arch 120 of denture teeth 122 positioned over ridge 110 of denture base material 100. As seen in FIG. 5A, pre-set arch 120 is oriented such that a labial portion of pre-set arch 120 is aligned with a labial portion of ridge 110 of denture base material 100, and a buccal portions of pre-set arch 120 are aligned with the buccal portions of denture base material 100, based on model 2 of the patient's mouth. In some embodiments, any adjustments made to pre-set arch 120, either along the arch width or occlusal planes as described in FIGS. 3A and 3B, may be performed such that pre-set arch 120 may fit the shape of the patient's mouth. In some embodiments, additional adjustments to pre-set arch 120 may be performed such that pre-set arch 120 may fit adapted denture base material 100 correctly, however, this may not be needed in certain scenarios.

System 350 of FIG. 5B includes pre-set arch 120 impressed into denture base material 100. After pre-set arch 120 has been aligned and positioned about adapted denture base material 100, as seen in FIG. 5A, pre-set arch 120 may be impressed into denture base material 100 such that a channel is created fitting denture base portion 124 of pre-set arch 120. In some embodiments, a dental practitioner or dental laboratory technician may impress pre-set arch 120 into denture base material 100. However, it is also possible for an impressing device to apply a mechanical force to pre-set arch 120 that causes pre-set arch 120 to be impressed into denture base material 100. The channel will serve, in one embodiment, to align pre-set arch 120 in the shape and orientation for the desired denture occlusion to occur. For example, a channel may be formed along an occlusal surface of denture base material 100 having dimensions corresponding to denture base portion 124 of pre-set arch 120 of denture teeth 122.

The created channel may have any suitable shape corresponding to pre-set arch 120, and may be of any suitable depth within denture base material 120 such that pre-set arch 120 may be secured therein. In some embodiments, pre-set arch 120 may be impressed into denture base material 100 by a dental practitioner or dental laboratory technician, however, the impression may also occur mechanically via a impressing apparatus designed to impart an appropriate amount of force to pre-set arch 120 to create the channel within denture base material 100.

When pre-set arch 120 is impressed into denture base material 100 forming the channel, a seam 310 is formed along ridge 110 of denture base material 100. Seam 310 may, for example, run along an lingual and labial, anterior portion 128 and lingual and buccal, posterior portions 126 of pre-set arch 120 where pre-set arch 120 and denture base material 100 meet. In some embodiments, seam 310 may represent a discontinuity between pre-set arch 120 and denture base material 100, which may be aesthetically unpleasing as well as cause potential structural issues for the denture device.

In some embodiments, an additional amount of denture base material, which may be substantially similar to denture base material 100, may be added to seam 310 along the anterior portion 128 and/or posterior portions 126 where pre-set arch 120 and the channel within denture base material 100 meet. The additional amount of denture base material may serve to smooth out seam 310 such that the denture base material 100 appears to flow smoothly to pre-set arch 120. Thus, seam 310 may appear to have been removed, as the additional amount of denture base material may fill in seam 310 (a more detailed description may be seen with regards to FIG. 8B).

Figure 6A:
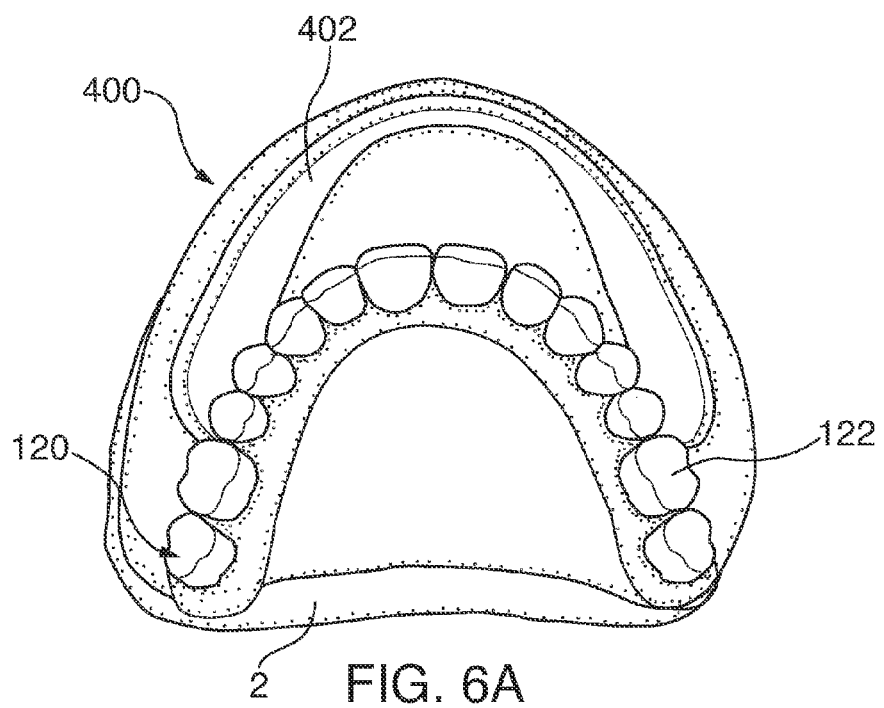
FIGS. 6A and 6B are illustrative diagrams of a pre-set arch of denture teeth being removed from an adapted amount of denture base material after a partial cure, and a channel formed within the adapted amount of denture base material, respectively, in accordance with various embodiments.
Figure 6B:
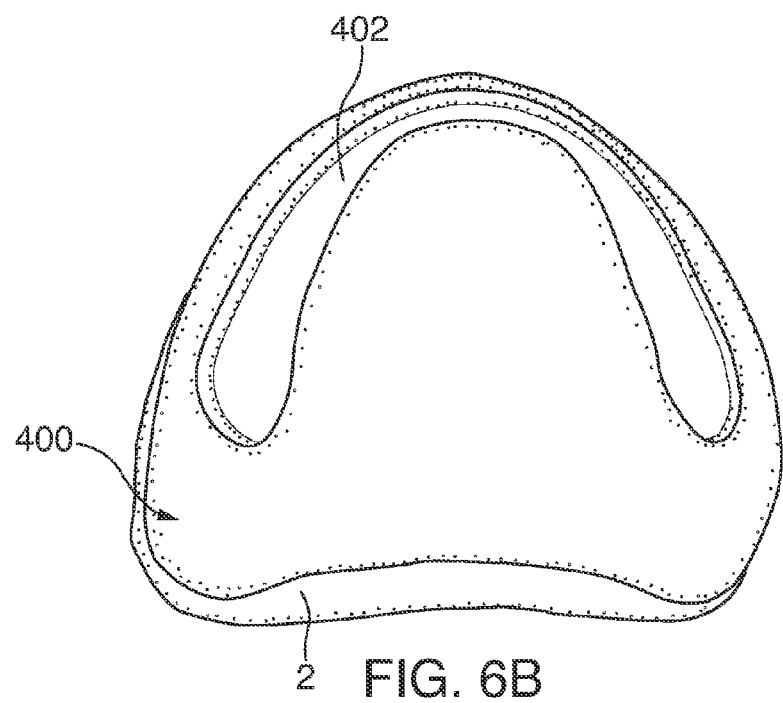

FIGS. 6A and 6B are illustrative diagrams of a pre-set arch of denture teeth being removed from an adapted amount of denture base material after a partial cure, and a channel formed within the adapted amount of denture base material, respectively, in accordance with various embodiments. In some embodiments, instead of applying a bonding agent to denture base portion 124 of pre-set arch 120 as seen in FIG. 4, a releasing agent may be applied to denture base portion 124. For example, as described above, a petroleum jelly or other lubricant may be applied to denture base portion 124 using brush 60. Persons of ordinary skill in the art will recognize that any releasing agent may be used, and different denture base materials may work better with different types of releasing agents, and the aforementioned example is merely exemplary. The releasing agent may, in some embodiment, help prevent pre-set arch 120 from being bonded to denture base material 100. In some embodiments, however, neither a bonding agent nor a releasing agent may be applied to denture base portion 124 of pre-set arch 120.

After pre-set arch 120 has been impressed into denture base material 100, as seen in FIG. 5B, pre-set arch 120 and denture base material 100 may be partially cured. For example, if denture base material 100 is a light-cure material, then denture base material 100 may be subjected to a certain intensity of UV or white (i.e. visible) light for a specific amount of time. For example, a tungsten halogen light bulb may be used to generate white light to cure denture base material 100. The amount of time and/or the intensity of the UV or white light that the uncured denture base material 100 is subjected to may determine an amount of curing that occurs. For example, subjecting uncured denture base material 100 to high-intensity white light for 2-3 minutes may partially cure denture base material 100, forming a partially cured denture device include partially cured denture base material 400 as seen in FIG. 6A.

Partially cured denture base material 400 of a partially cured denture device may, in some embodiments, be substantially rigid such that the partially cured denture device retains is capable of retaining its shape, but allows pre-set arch 120 to be removed. For example, as seen in FIG. 6A, pre-set arch 120 is removed from partially cured denture base material 400 of the partially cured denture device, leaving channel 402 formed therein. In some embodiments, denture base material 100 may be fully cured or not cured at all. For example, denture base material 400 may have been cured to any suitable level such that pre-set arch 120 may be removed without denture base material 400 loosing shape and form. In some embodiments, as described above, use of a releasing agent on denture base portion 124 of pre-set arch 120 may allow for pre-set arch 120 to be easily removed from partially cured denture base material 400.

In some embodiments, however, instead of partially curing denture base material 100, denture base material may be fully cured such that it is substantially rigid. In this particular scenario, instead of applying a bonding agent to denture base portion of pre-set arch 120, a releasing agent may be applied. This may allow a dental practitioner or laboratory technician to remove pre-set arch 120 from fully cured denture base material (e.g., denture base material 612) such that adjustments to pre-set arch 120 may occur.

After pre-set arch 120 has been removed from partially cured denture base material 400, as seen in FIG. 6B, channel 402 may be analyzed. In some embodiments, a dental practitioner or dental laboratory technician may analyze channel 402 to determine a quality of channel 402 (e.g., the impression made) and/or one or more dimensional parameters of channel 402. For example, a dental practitioner or dental laboratory technician may determine whether or not channel 402 is structure stable enough to hold pre-set arch 120 when it is to be bonded thereto. If, for example, one or more portions of partially cured denture base material 400 adheres to denture base portion 124 of pre-set arch 120, then when pre-set arch 120 is removed, the one or more portions may be removed from with pre-set arch 120. Thus, there may be portions of the denture device formed by partially cured denture base material which are substantially thin, or there may be one or more holes in channel 402. As another example, a dental practitioner or dental laboratory technician may measure the dimensions of channel 402 along the anterior and/or posterior sections of channel 402 to determine whether or not, after pre-set arch 120 has been removed, channel 402 has retained the proper shape, size, and/or orientation of pre-set arch 120.

In some embodiments, pre-set arch 120 may be placed back into channel 402, and the denture device including partially cured denture base material 400 and pre-set arch 120 may be placed in a patient's mouth to test the fit of the denture device. In some embodiments, this may be referred to as a "try-in". The try-in may allow both the dental practitioner and the patient to determine whether or not the partially cured denture device, as formed thus far, looks, feels, and functions correctly. If the patient and/or dental practitioner is/are unsatisfied with the try-in, a new bite registration using the partially cured denture device including partially cured denture base material 400 may be obtained. After the new bite registration is obtained, the dimensions of channel 402 and/or a shape and/or amount of base material 121 of pre-set arch 120 may be adjusted. For example, an adjustment to an amount d of the arch width and/or an amount l of the occlusal plane of pre-set arch 120 may be made by the dental practitioner or dental laboratory technician such that pre-set arch 120 has a better fit within a new occlusal scheme as defined by the new bite registration. However, it is also possible for another try-in to occur at this point as well.

If, however, at this stage, the dental practitioner and/or patient is/are satisfied with the adjusted pre-set arch 120, pre-set arch 120 may be removed from channel 402 within partially cured denture base material 400 and a bonding agent, such as methyl methacrylate monomer, may be applied to denture base portion 124 of pre-set arch 120. For example, after denture base material 100 of FIG. 5A or 5B has been cured to create a partially cured denture device including partially cured denture base material 400 having channel 402, pre-set arch 120 may be removed. After pre-set arch 120 has been removed, the bonding agent may be applied to denture base portion 124 of pre-set arch 120.

Figure 7:
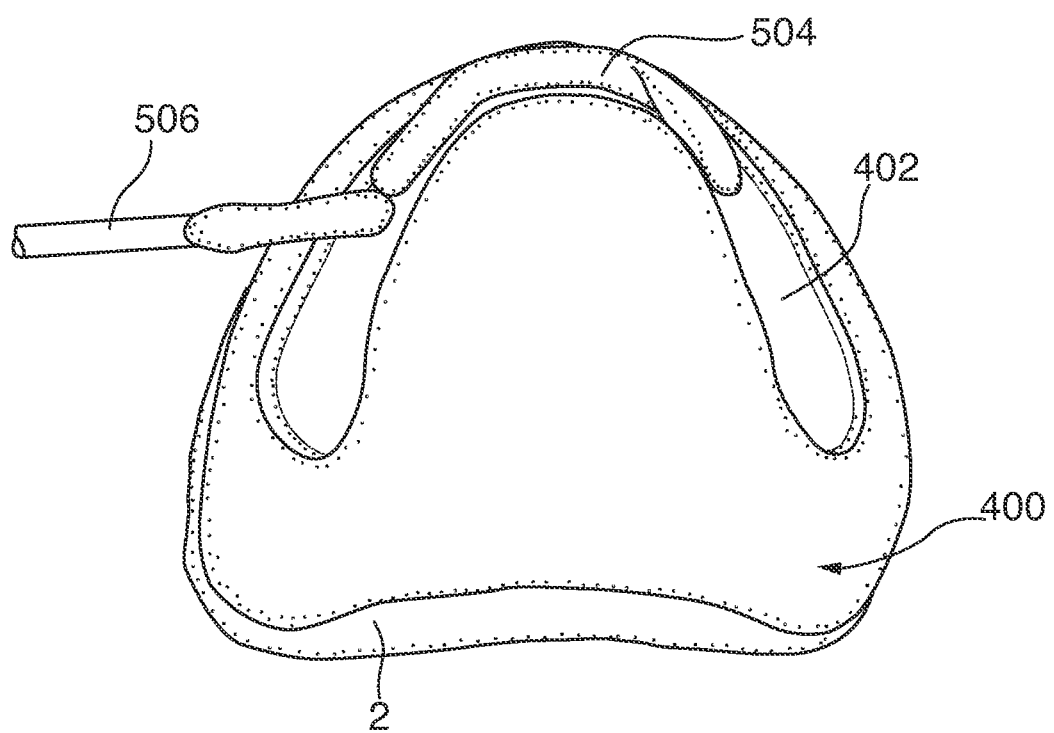
FIG. 7 is an illustrative diagram of an additional amount of denture base material applied to the channel within the adapted denture base material in accordance with various embodiments.

FIG. 7 is an illustrative diagram of an additional amount of denture base material applied to the channel within the adapted denture base material in accordance with various embodiments. In some embodiments, partially cured denture base material 400 may have an additional bonding agent 504 applied to channel 402. For example, in preparation for bonding pre-set arch 120 to partially cured denture base material 400, a dental practitioner or dental laboratory technician may apply a bonding agent 504 to along an inner surface of channel 402. Bonding agent 504 may, in some embodiments, be substantially similar to the bonding agent applied to denture base portion 124, as described above. In some embodiments, bonding agent 504 may be made of an uncured amount of denture base material, similar to denture base material 100.

If bonding agent 504 is substantially similar to the bonding agent used on denture base surface 124 of pre-set arch 120, then a brush, similar to brush 60 of FIG. 4, may be used. However, in some embodiments, a different bonding agent 504 may be applied to channel 402 using apparatus 506. For example, if bonding agent 504 is an amount of uncured denture base material 100, then a substantially flat plastic or metallic apparatus 506 may be used to apply bonding agent 504 to channel 402. Persons of ordinary skill in the art will recognize that any amount of bonding agent 504 may be used to aid in bonding pre-set arch 120 to partially cured denture base material 400 of the denture device.

Figure 8A:
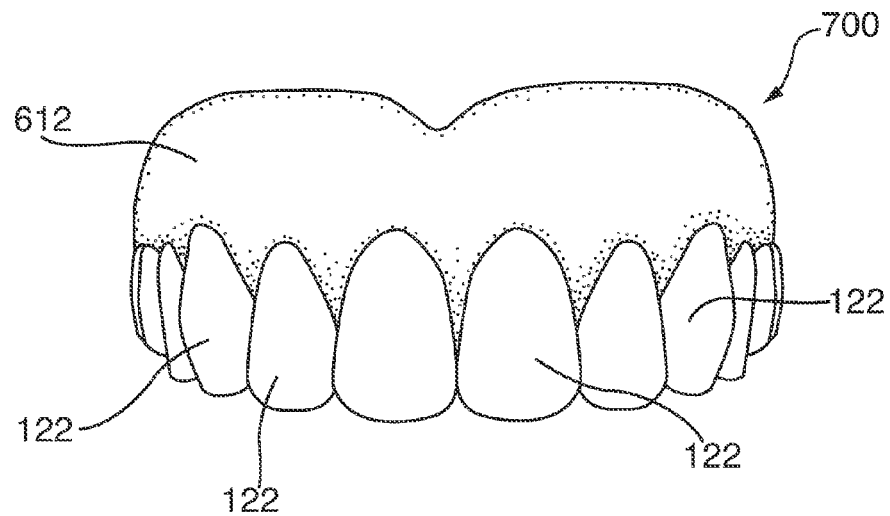
FIG. 8A is an illustrative diagram of a front view of a denture device that is polished and trimmed to remove any extraneous material in accordance with various embodiments.

FIG. 8A is an illustrative diagram of a front view of a denture device that is polished and trimmed to remove any extraneous material in accordance with various embodiments. Denture device 700 of FIG. 8A may include teeth 122 and denture base portion 612. In some embodiments, after bonding agent 504 has been applied to channel 402, as seen in FIG. 7, pre-set arch 120 of denture teeth 122 may be pressed into channel 402. For example, pre-set arch 120 may be pressed into channel 402 in a similar manner as seen in FIG. 5B, with the exception that the later may be in preparation for a final setting of pre-set arch 120.

In some embodiments, an additional amount of denture base material may be applied to the labial and/or buccal and/or lingual portions of pre-set arch 120 and/or partially cured denture base material 400 such that a seam, such as seam 310, about channel 402 is alleviated. By applying the additional amount of denture base material to the seam, the transition from pre-set arch 120 to denture base material 400 may appear to be removed. This may enhance the look of a denture device that will be formed (e.g., denture device 700), as well as increase the structural integrity of the finished denture device, as the additional denture material may serve to secure pre-set arch 120 in channel 402 of denture base material 400.

After pre-set arch 120 has been placed back into channel 402 and the additional denture base material has been applied to the seam about pre-set arch 120, partially cured denture base 400 and pre-set arch 120 may be cured for a second amount of time. For example, partially cured denture base 400 and pre-set arch 120 may be placed in under a high-intensity white light for a certain amount of time such that partially cured denture material 400 and the additionally applied denture base material become substantially rigid forming denture base portion 612. For example, partially cured denture base material 400 may, when placed under a high-intensity white light for 7-8 minutes, become rigid, or fully cured. However, persons of ordinary skill in the art will recognize that the aforementioned amount of time is merely exemplary. In some embodiments, partially cured denture base material 400 may be left to self-polymerize for a certain amount of time to become hardened, thus forming denture base portion 612. For example, partially cured denture base material 400 may be left to self-polymerize for 7-8 minutes, however the self-polymerization time may be more or less time depending on the type and amount of denture base material 400 used.

In some embodiments, if, after the second cure, it is determined that pre-set arch 120 is not adequately secured to denture base 612, another additional amount of denture base material may be applied substantially about where pre-set arch 120 and denture base 612 meet. In this scenario, a third curing of the denture base 612, pre-set arch 120, and additional denture base material may occur. This process may be repeated until the resulting denture device has a suitable look, feel, and structural integrity needed for use by a patient.

In some embodiments, after the second cure, denture device 700 may be formed. Denture device 700 may, in some embodiments, be substantially rigid such that will retains its shape and structure when used by a patient. However, after the second curing occurs, a dental practitioner or dental laboratory technician may trim and/or polish denture device 700. For example, if there is any excess denture material that will interact or irritate a patient's mouth, the practitioner or laboratory technician may trim or file down that section or sections such that denture device 700 has a comfortable feel. Furthermore, any minor imperfections or areas that may have a poor finish may be polished to enhance their appearance. For example, if a small amount of denture base material has seeped on a portion of one or more teeth 122, then a practitioner or laboratory technician may polish that portion of teeth 122 to remove the denture base material, making teeth 122 shine and appear aesthetically appealing. However, the polishing and/or trimming of denture device 700 is optional, and in some embodiments may not be needed.

In some embodiments, referring back to FIG. 5B, it may be determined that one or more try-ins are not needed, and denture base material 100 may be cured to form denture device 700. For example, if pre-set arch 120 of FIG. 5B fits model 2 correctly, then a practitioner may simply apply additional denture base material to remove seam 310 from the anterior and posterior portions 128 and 126, respectively. Then, system 350 may be cured (e.g., using high-intensity white light or allowing to self-polymerize), such that denture device 700 is formed. Furthermore, as mentioned above, denture device 700 may then be trimmed and/or polished to remove any imperfections of denture device 700. For example, if additional amounts of denture base material are required to be used to aid in securing pre-set arch 120, this material may need to be trimmed or polished away such that pre-set arch 120 has a natural look and feel.

Figure 8B:
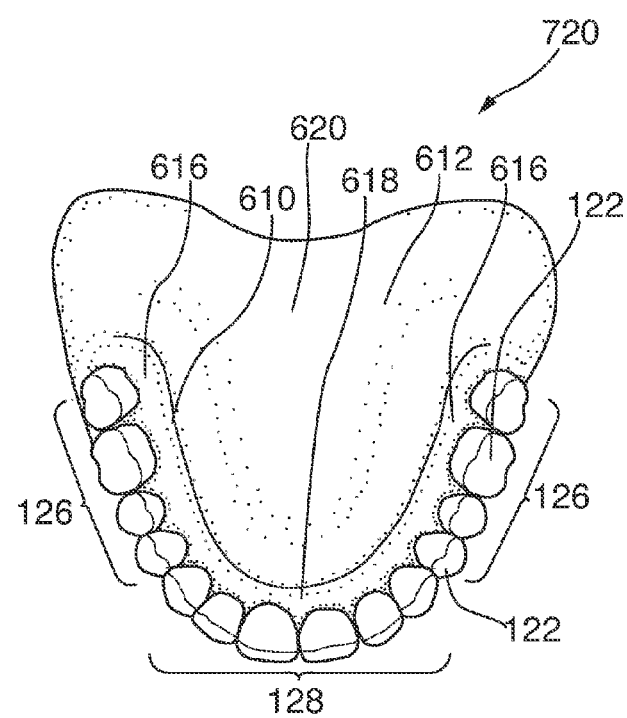
FIG. 8B is an illustrative diagram of a bottom view of a denture device including an additional amount of denture base material applied to a seam formed between a channel and the pre-set arch of denture teeth in accordance with various embodiments.

FIG. 8B is an illustrative diagram of a bottom view of a denture device including an additional amount of denture base material applied to a seam formed between a channel and the pre-set arch of denture teeth in accordance with various embodiments. Denture device 720 of FIG. 8B includes, in some embodiments, teeth 122 and cured denture base material 612. As described previously, teeth 122 may include anterior portion 128 and posterior portions 126. After pre-set arch 120, for instance of FIG. 5B, has been impressed into denture base material 100 or 400 (depending on whether or not a partial curing is to occur), a dental practitioner or dental laboratory technician may add an additional amount of denture base material along seam 310 where channel 402 and pre-set arch 120 meet.

In some embodiments, the additional denture base material may be added along the lingual and/or labial surface of the anterior seam 618 and/or the lingual and/or buccal surface of posterior seam 616. For example, the additional denture base material may be added prior to a final curing of denture device 720. The additional denture base material may therefore be used to smooth out a transition region 610 between pre-set arch 120 of denture teeth 122 and a palate portion 620 of denture base 612. However, persons of ordinary skill in the art will recognize that palate portion 620 of denture base 612 may instead be replaced by a lower mandible portion if denture device 720 corresponds to a lower denture device.

After the additional denture base material has been added along the lingual and/or labial surface of the anterior seam 618 and/or the lingual and/or buccal surface of posterior seam 616, denture device may be cured to form a final denture device, such as denture device 700 of FIG. 8A. In some embodiments, denture device 720 may be subjected to high-intensity white light for a certain amount of time to cure the newly added denture base material. For example, if the denture base material is a light-cure material, a dental practitioner or dental laboratory technician may subject denture device to a high-intensity white light in order to harden the denture base material. In some embodiments, however, the additional denture base material may cure after being left to self-polymerize for a certain amount of time.

Figure 8C:
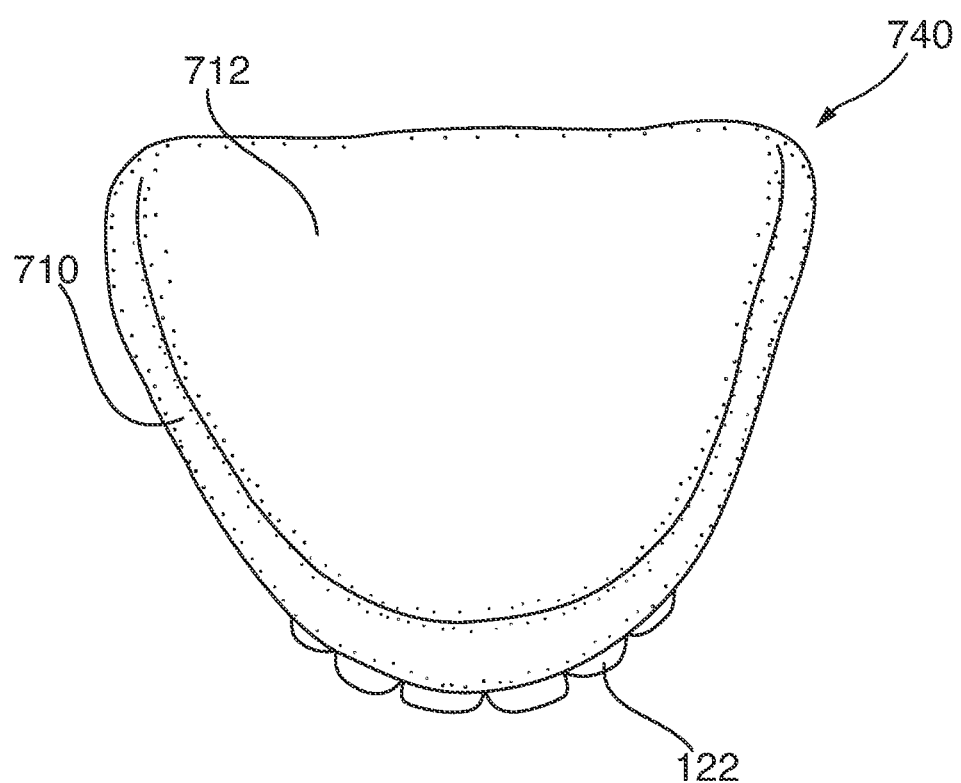
FIG. 8C is an illustrative diagram of a top view of a denture device, such as the denture device of FIG. 8B, in accordance with various embodiments.

FIG. 8C is an illustrative diagram of a top view of a denture device, such as the denture device of FIG. 8B, in accordance with various embodiments. Denture device 740, in some embodiments, may correspond to an overhead view of denture device 700 or 720 of FIGS. 8A and 8B, respectively. Denture device 740 may include upper palate portion 712 in some embodiments. Upper palate portion 712 may correspond to a portion of denture device 740 that will be in contact with a roof of a patient's mouth. However, persons of ordinary skill in the art will recognize that denture device 740 may correspond to either an upper or lower mandibular denture device, and palate portion 712 may instead correspond to a portion of denture device 740 that may be in contact with a patient's tongue or other portion of the patient's mouth.

Denture device 740 may also include ridge 710. Ridge 710 may correspond to a portion of denture device 740 that is placed proximate to a patient's gums. For example, a patient may insert denture device 740 into their mouth such that ridge 710 is between the patient's lip (e.g., upper lip) and the patient's gums. The palate portion 712, in one illustrative example, may then contact the roof of the patient's mouth. Thus, with the aforementioned orientation, when a patient attempts to smile, teeth 122 of denture device 740 are visible.

In some embodiments, some or all of palate portion 712 may be removed such that denture device 740 is substantially arch shaped. For example, a dental practitioner or dental laboratory technician may trim away portions of denture device 740 such that denture device 740 still resides between a patient's gums and lip, when inserted, but only a portion of palate portion 712 will contact the roof of the patient's mouth.

Figure 9:
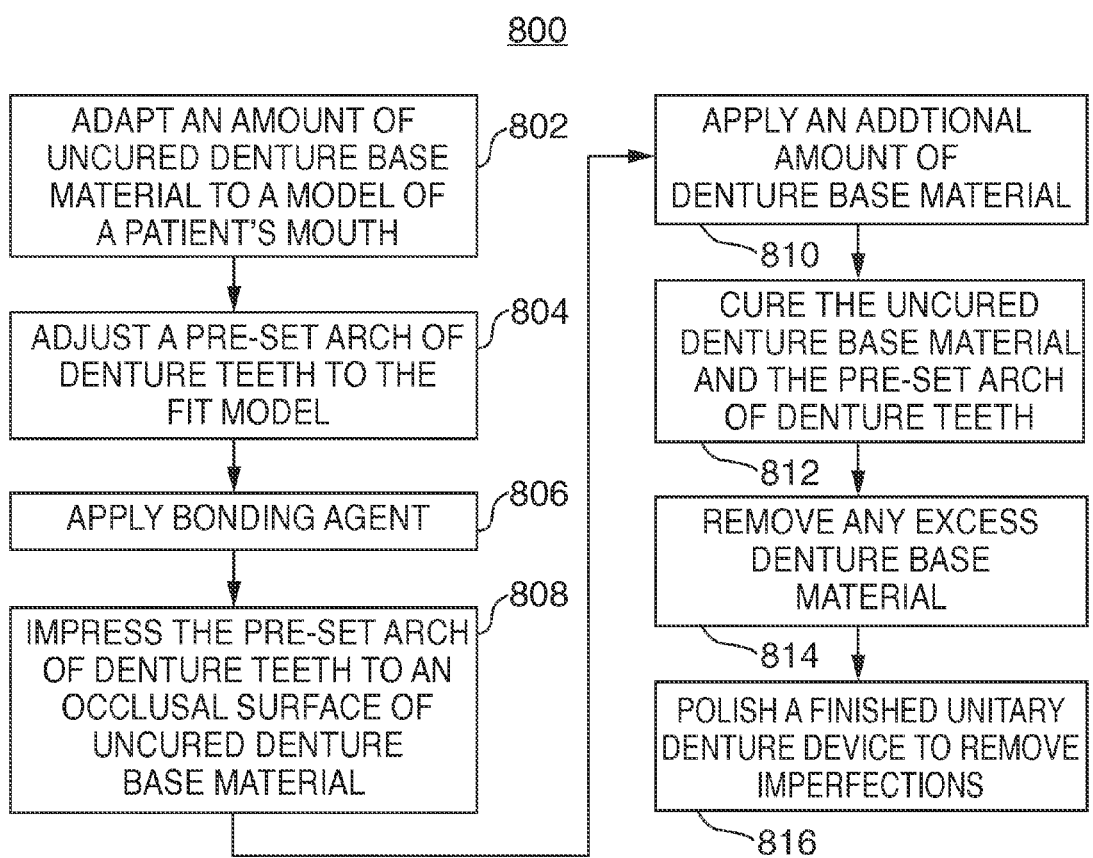
FIG. 9 is an illustrative flowchart of a process for forming a denture device in accordance with various embodiments.

FIG. 9 is an illustrative flowchart of a process for forming a denture device in accordance with various embodiments. Process 800 may begin at step 802. At step 802, an amount of uncured denture base material may be adapted to a model of a patient's mouth. For example, a 3-D scan, impression, or bite registration may be taken of a patient seeking to obtain dentures. As an illustrative example, model 2 of FIG. 1 may be obtained, which includes ridge 10 corresponding to where a user's gums are, and inner portion 12 corresponding to where a palate portion or lower mandibular portion of a patient's mouth. After model 2 of the patient's mouth is obtained, uncured denture base material 100 of FIG. 2 may be adapted to fit about model 2. For example, denture base material 100 may be placed onto model 2 and adapted such that ridge portion 110 and inner portion 112 substantially fit model 2. In some embodiments, excess denture base material 114 may be adapted to fit excess portion 14 of model 2, however the amount of excess denture base material 114 may vary.

At step 804, a pre-set arch of denture teeth may be adjusted to fit the model of the patient's mouth. For example, pre-set arch 120 may include a full set, or a partial set, of denture teeth 122. The number of denture teeth included in pre-set arch 120 may depend, in some embodiments, on the specific patient case, as some patients may need a full set of teeth 122 for their denture device, and some patients may need only a partial set of teeth 122 for their denture device.

In some embodiments, pre-set arch 120 may be heated to a first temperature to enable a dental practitioner to adjust pre-set arch. For example, after placing pre-set arch 120 in boiling water (e.g., at least 100-degrees Celsius), pre-set arch 120 may become malleable. An arch width of pre-set arch 120 may be adjusted by an amount d as seen in FIG. 3A such that the arch width extends towards or away from midline on either side of pre-set arch 120. For example, one occlusal side of pre-set arch 120 may be adjusted in a first direction (e.g., inwards, outwards), while the other occlusal side of pre-set arch 120 may be adjusted in a second direction. In some embodiments, the first direction may extend towards a midline of pre-set arch 120 while a second direction may extend away from midline.

In some embodiments, an occlusal plane (on either side) of pre-set arch 120 may be adjusted by an amount l as seen in FIG. 3B. For example, either occlusal portion of pre-set arch 120 may be adjusted such that that occlusal portion is adjusted upwards (e.g., towards an upper portion of a patient's mouth) or downwards (e.g., towards a lower portion of a patient's mouth) by an amount l. The amount l that pre-set arch 120 is adjusted for either occlusal portion may differ or may be similar such that one occlusal portion is adjusted by a first amount, and the other occlusal portion is adjusted a second amount. Either occlusal portion of pre-set arch 120 may also be adjusted such that the posterior teeth are rotated outwards (e.g. toward the cheek or lips) or inwards (e.g. toward the tongue). In some embodiments, an amount of base material 121 of pre-set arch 120 may be reshaped or removed. In some embodiments, the adjustments along the arch width and/or occlusal planes and/or base material 121 may be made to accommodate existing dentition on an opposing arch or on an opposing portion of a patient's mouth.

After pre-set arch 120 has been adapted to fit model 2 of the patient's mouth in the desired occlusion, and uncured denture base material 100 has been adapted to fit model 2, process 800 may proceed to step 806. At step 806, a bonding agent may be applied to pre-set arch 120. For example, a bonding agent, such as methyl methacrylate monomer, may be applied to denture base portion 124 of pre-set arch 120. In some embodiments, a bonding agent may also be applied to a portion of denture base material 100, such as ridge 110, where pre-set arch 120 will be placed on denture base material 100. For example, an additional amount of denture base material may be applied along ridge 110 substantially where pre-set arch 120 will be placed.

At step 808, pre-set arch 120 including the bonding agent applied thereto may be impressed to an occlusal surface of uncured denture base material 100. For example, as seen in FIG. 5B, pre-set arch 120 may be impressed into denture base material 100. In some embodiments, a dental practitioner or dental laboratory technician may manually impress pre-set arch 120 into denture base material 100. For example, a dental practitioner or dental laboratory technician may press pre-set arch 120 into denture base material using their hands or a handheld or hand operated tool that applies adequate force to pre-set arch 120 such that it is impressed into uncured denture base material 100. As another example, a mechanical or electronic impressing device may be used to impress pre-set arch 120 into denture base material 100 such that a suitable force is used.

In some embodiments, pre-set arch 120 may be positioned and aligned over uncured denture base material 100 prior to being impressed. For example, as seen in FIG. 5A, pre-set arch 120 may be positioned about ridge 110 of uncured denture base material. Pre-set arch 120 may additionally be aligned such that pre-set arch 120 has a proper orientation with respect to model 2 of the patient's mouth. In some embodiments, one or more markers may be used in conjunction with model 2 such that, when uncured denture base material 100 is adapted thereto, a position and orientation of pre-set arch 120 may be known to aid in properly aligning pre-set arch 120 to model 2.

At step 810, an additional amount of denture base material may be applied along a seam formed when pre-set arch 120 is impressed into denture base material 100. For example, when pre-set arch 120 is impressed, a channel, such as channel 402 of FIGS. 5A and 5B, may be formed. Seam 310 may correspond to a portion of the channel that is visible when pre-set arch 120 resides within the channel. For example, seam 310 may run along the lingual and/or labial surface of an anterior portion 128 and/or the lingual and/or buccal surface of posterior portions 126 of pre-set arch 120 where pre-set arch 120 meets inner portion 112 of denture base material 100. In some embodiments, no additional denture base material may be needed, and step 810 may be omitted.

After any additional denture base material has been applied, process 800 may proceed to step 812. At step 812, uncured denture base material 100, pre-set arch 120 impressed into uncured denture base material 100, and any additional denture base material may be cured. In some embodiments, uncured denture base material 100 may be a light-cure material or an auto-polymerizing material. For example, if denture base material 100 is a light-cure material, then curing may correspond to applying a UV light or a high intensity white light to denture base material 100 for a certain amount of time. As another example, if denture base material 100 is an auto-polymerizing material, then denture base material may allowed to auto-polymerize for a certain amount of time such that denture base material 100 hardens and sets.

At step 814, any excess denture base material left after curing of the denture base material may be removed. For example, excess denture base material 114 of FIG. 2 may, in some embodiments, have remained when curing occurred at step 812. After curing, excess denture material 114 may now remain, however, in a cured state. In some embodiments, a dental practitioner or dental laboratory technician may remove the excess, now cured, denture base material by trimming or filing away the excess material. The amount of material removed may correspond to any amount of denture material so long as the cured denture device, such as denture device 700, 720, and/or 740, remains structurally stable and is capable of fitting within the patient's mouth comfortably.

At step 816, a unitary denture device, such as denture device 700, 720, and/or 740 of FIGS. 8A, 8B, and 8C, respectively, may be polished. Polishing of the denture device may remove any imperfections, such as bumps or grooves, within the denture device. For example, a small amount of denture base material may reside on one or more teeth 122. After curing, the denture base material has become rigid, which may impede the use of the one or more teeth 122. A dental practitioner may, in the exemplary embodiment, polish away the excess material. For example, the dental practitioner may use a pumice paste applied using brushes, buffs, felt cones, or any other apparatus capable of polishing. In one scenario, the polishing may occur on a table, bench-mounted, resting, or potentially hand-held grinder or buffer machine)]]

In some embodiments, steps 814 and 816 may occur at a substantially same time. For example, the unitary denture device may be trimmed and polished by a dental practitioner or dental laboratory technician at a substantially same time to ensure that the fit and look of the denture device is correct. In some embodiments, however, steps 814 and/or 816 may be omitted.

Figure 10A:
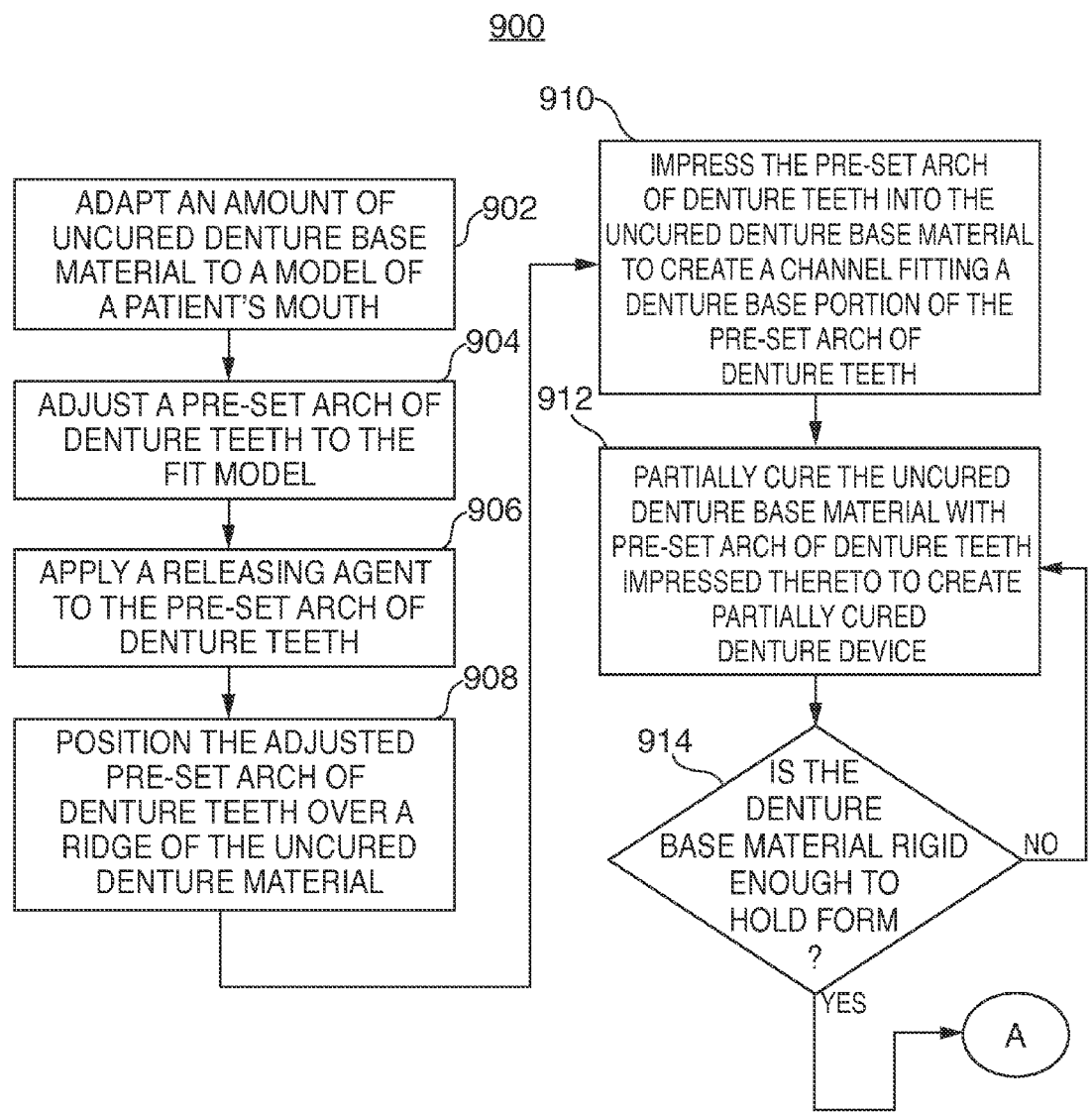
FIGS. 10A-C are illustrative flowcharts of another process for forming a denture device in accordance with various embodiments.
Figure 10B:
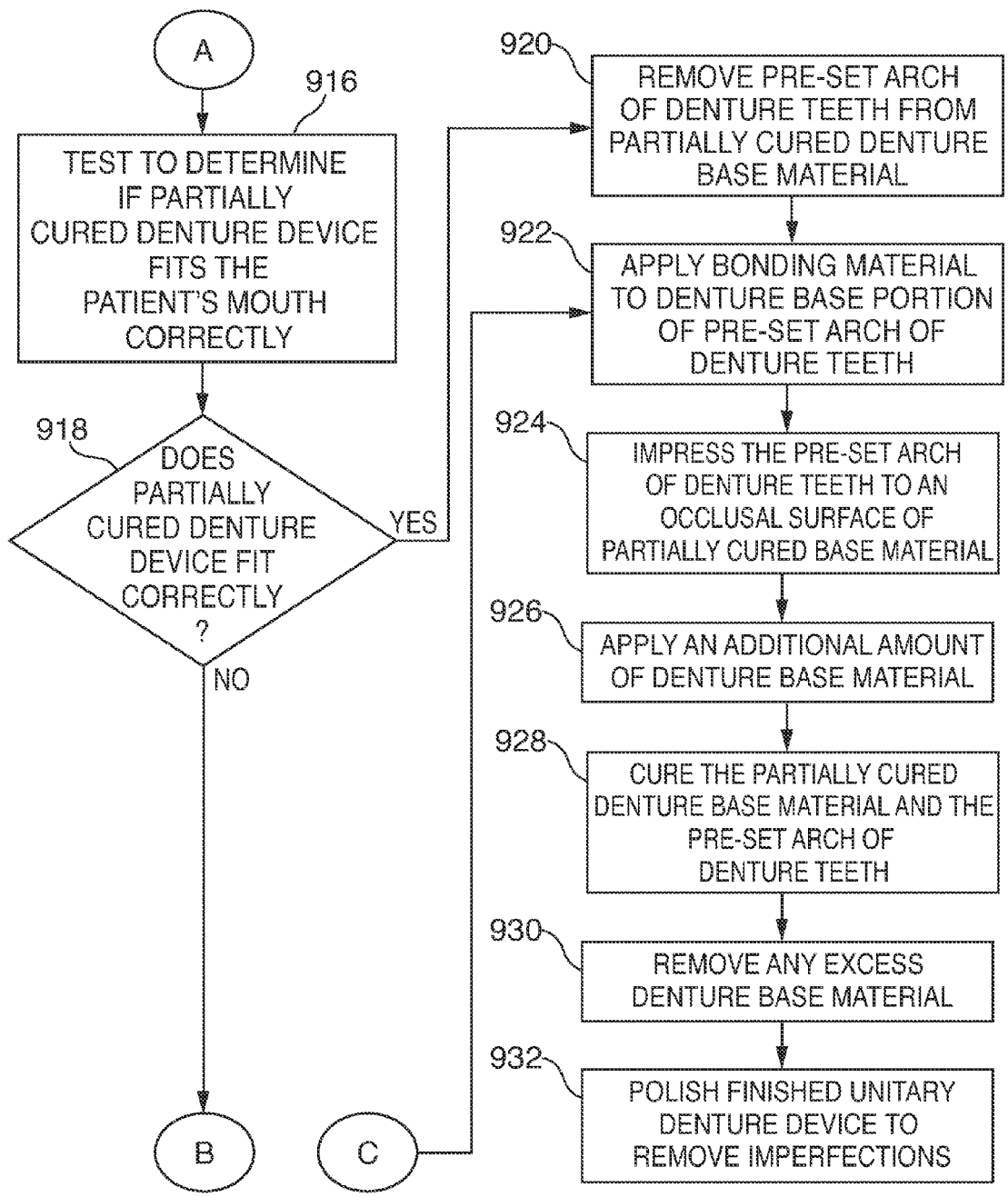
Figure 10C:
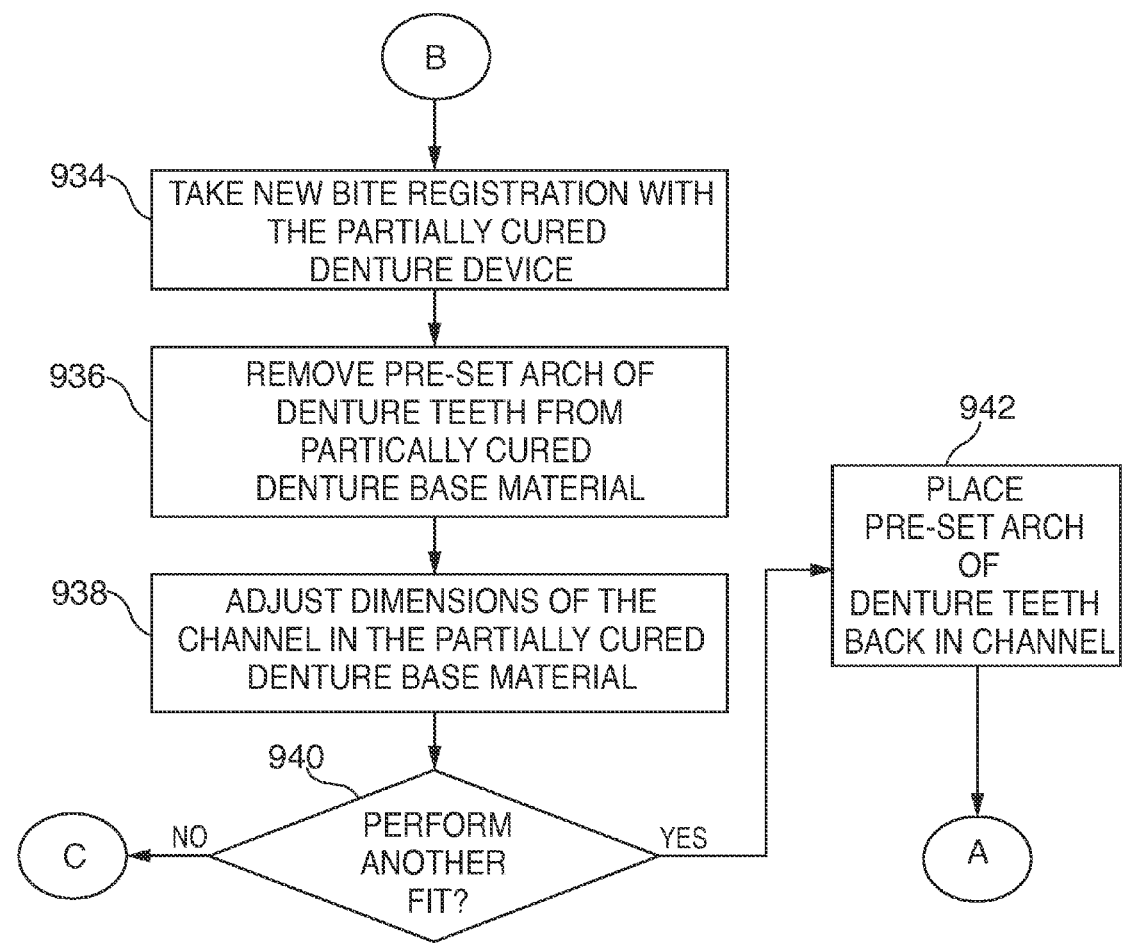

FIGS. 10A-C are illustrative flowcharts of another process for forming a denture device in accordance with various embodiments. Process 900 may begin at step 902. At step 902, an amount of uncured denture base material may be adapted to a model of a patient's mouth. At step 904, a pre-set arch of denture teeth may be adjusted to fit the model of the patient's mouth. In some embodiments, steps 902 and 904 of process 900 may be substantially similar to steps 802 and 804 of process 800, and the previous description may apply.

At step 906, a releasing agent may be applied to a denture base portion of the pre-set arch. For example, brush 60 of FIG. 4 may apply a releasing agent, such as a petroleum jelly or other lubricant, to denture base portion 124 of pre-set arch 120. The releasing agent may allow a dental practitioner or dental laboratory technician to remove pre-set arch 120 from uncured denture base material 100 without causing any unintended bonding to occur between denture base material 100 and pre-set arch 120.

After the releasing agent has been applied to pre-set arch 120, pre-set arch 120 may be positioned over a ridge of the uncured denture base material at step 908. In some embodiments, pre-set arch 120 may be oriented over ridge 110 of denture base material 100 such that pre-set arch 120 aligned with model 2 of the patient's mouth. By positioning pre-set arch 120 prior to augmenting uncured denture base material 100 (e.g., by impressing), a dental practitioner or dental laboratory technician may increase the probability of having a correct and properly fitting denture device.

At step 910, pre-set arch 120 may be impressed into uncured denture base material 100. When impressed into denture base material 100, pre-set arch 120 may create a channel, such as channel 402, within uncured denture base material 100. Channel 402 may, in some embodiments, represent and be formed in a shape of a denture base portion (e.g., denture base portion 124) of pre-set arch 120. In some embodiments, step 910 of process 900 may be substantially similar to step 808 of process 800, and the previous description may apply. Persons of ordinary skill in the art will also recognize that, in some embodiments, steps 908 and 910 may occur at a substantially same time. For example, pre-set arch 120 may be positioned atop denture base material 100 and impressed therein to create a channel in one step.

At step 912, uncured denture base material 100 including pre-set arch 120 impressed therein may be partially cured such that a partially cured denture device is formed. In some embodiments, if denture base material 100 is a light-cure material, a partial cure of denture base material 100 may include applying a high-intensity white light to denture base material for a first amount of time (e.g., 2-3 minutes). However, if denture base material 100 is auto-polymerizing material, a partial cure may correspond to allowing denture base material 100 and pre-set arch 120 to sit unimpeded for a second amount of time (e.g., 10-15 minutes). Persons of ordinary skill in the art will recognize that any amount of time may enable a partial cure of denture base material 100 to occur.

At step 914, a determination is made as to whether or not denture base material 100 is rigid enough to hold its form. For example, the partial cure at step 912 may or may not enable the partially cured denture device to retain the shape of model 2 of the patient's mouth and/or retain the pre-set arch 120 impressed therein. If, at step 914, it is determined that the partial cure performed at step 912 did not cure denture base material 100 such that denture base material 100 will retain its form (and pre-set arch 120 impressed therein), process 900 may return to step 912 and another partial cure may occur. For example, denture base material may be subjected to high-intensity white light again for a third amount of time (e.g., 2-3 minutes). In some embodiments, however, the additional partial cure may be of a same amount of time as the first partial (e.g., 5-10 minutes).

If, however, at step 914, it is determined that partially cured denture material 400 of created partially cured denture device is rigid enough to hold its shape and/or form, process 900 may proceed to step 916. At step 916, a test may be performed to determine if partially cured denture device 400, for example, fits correctly within the patient's mouth. This portion of process 900 may be referred, in some embodiments, to a "try-in". With a try-in, partially cured denture device 400 may be placed within the patient's mouth such that a dental practitioner may asses the fit and function of the denture device, and the patient may asses the feel of the denture device. This may be particularly useful in that a dental practitioner and/or patient may be able to determine an accuracy of the look, fit, and feel of the denture device prior to it being fully formed. At this point, as detailed below, additional modifications may be capable of being performed, which is a distinct advantage over previously used techniques where a fully formed denture device would be made in a laboratory, tested on the patient, and if modification where needed, the denture would have to be sent back out to the laboratory for a more extensive reconstruction. Thus, a try-in device comprising a denture arch that may be removed from a denture base, where either or both of these components may be modified to more readily to fit a new occlusal scheme, may significantly reduce an amount of time, and potential cost, associated with obtaining a properly fitting and functioning denture device.

At step 918, a determination may be made as to whether or not partially cured denture device 400, as tested on the patient, fits correctly. As mentioned above, this may be part of the try-in process. For example, the dental practitioner may determine if the partially cured denture device fits correctly by assessing midline, planes, vertical dimension of occlusion, centric relation, aesthetics, phonetics, and aesthetics, however persons of ordinary skill in the art may use any suitable criteria for determining an accuracy of the fit. If the denture device fits correctly, then process 900 may proceed to step 920.

At step 920, pre-set arch 120 may be removed from partially cured denture base material 400. For example, as seen in FIGS. 6A and 6B, a dental practitioner or dental laboratory technician may remove pre-set arch 120 from partially cured denture base material 400. Removing pre-set arch 120 may allow the dental practitioner or dental laboratory technician to view and analyze a shape and form of channel 402. For example, a dental practitioner or dental laboratory technician may look to make sure channel 402 has a proper shape and size for pre-set arch 120 when it will be bonded back. The dental practitioner or dental laboratory technician may also determine whether or not any structural aspects of the partially cured denture device have been compromised. For example, if after removing pre-set arch 120, it is determined that channel 402 includes one or more holes or defects, the practitioner or laboratory technician may be able to note these issues and address them. In one exemplary instance, an amount of denture base material may be applied to channel 402 to correct any holes or defects found upon removal of pre-set arch 120.

In some embodiments, instead of partially curing denture base material 100, denture base material 100 may be fully cured. In this particular scenario, a removing agent may still be applied to denture base portion 124 of pre-set arch 120, however, once fully cured, pre-set arch 120 may be removed from the fully cured denture base material. For example, minor adjustments to an arch width or occlusal planes of pre-set arch 120 may occur after a partial cure of denture base material 100 by removing pre-set arch 120 from the fully cured denture base material.

At step 922, a bonding agent may be applied to denture base portion 124 of pre-set arch 120. For example, a bonding agent, such as methyl methacrylate monomer, may be applied. In some embodiments, an additional bonding agent, such as an additional amount of uncured denture base material 100, may applied to channel 402 of partially cured denture base material 400 in addition to, or instead of, a bonding agent being applied to denture base portion 124 of pre-set arch 120. The additional denture base material may thus serve as a bonding agent by hardening and bonding pre-set arch 120 to partially cured denture base 400 in response to a curing being performed. In some embodiments, step 922 of process 900 may be substantially similar to step 806 of process 800 and the previous description may apply.

After a bonding agent is applied at step 922, pre-set arch 120 may be impressed into an occlusal surface of partially cured denture base material 400 at step 924. For example, pre-set arch 120 may be impressed into channel 402. An additional amount of denture base material may then be applied to a seam that is formed along channel 402 where pre-set arch 120 and channel 402 meet. The additional amount of denture base material may smooth out and remove the seam, such as seam 310, and improve the structure integrity of the denture device by further securing pre-set arch 120 to the denture device. At step 928, an additional cure may be performed to the partially cured denture device including partially cured denture base material 400, pre-set arch 120 impressed into the occlusal surface of denture base material 400, and any additional denture base material that may be applied. For example, the partially cured denture device may be subject to a high-intensity white light or a UV light for a fourth amount of time (e.g., 7-8 minutes). After the additional curing has been performed, any excess denture base material may be removed at step 930, and a unitary denture device that has now been formed may be polished to remove any remaining imperfections at step 932. In some embodiments, steps 922-932 of process 900 may be substantially similar to steps 806-816 of process 800, and the previous description may apply.

If, however, at step 918, it is determined that the partially cured denture device does not fit correctly within the patient's mouth, process 900 may proceed to step 934. At step 934, a new bite registration may be taken with the partially cured denture device. For example, a reorientation of the partially cured denture device within the patient's mouth to attempt to place it in proper occlusion along, as well as recording that new occlusion may occur to obtain the new bite registration. This information may then be used to reorient the model, which may, in some embodiments, be mounted to a device called an articulator, which holds the model in a specific orientation in space which matches the desired occlusal scheme In some embodiments, however, a user may choose to CAD and/or CAM create a new model of the patient's mouth using the information obtained with the new bite registration.

After a new bite registration has been taken, pre-set arch 120 may be removed from partially cured denture material 400. In some embodiments, step 936 may be substantially similar to step 920, and the previous description may apply.

After pre-set arch 120 has been removed, any adjustments needed to be made to channel 402 and/or pre-set arch 120 based on the information obtained from the new bite registration may be made at step 938. For example, channel 402 may be widened or lengthened to better accommodate denture base portion 124 of pre-set arch 120 in the desired orientation of occlusion. In some embodiments, additional denture base material 100 may be applied to channel 402 to repair any holes or defects discovered in response to removal of pre-set arch 120, as well as to adjust the dimensions of channel 402. In some embodiments, however, in addition to, or instead of, adjusting channel 402, a dental practitioner or laboratory technician may adjust pre-set arch 120 to a desired orientation for occlusion.

At step 940, a determination of whether or not another fit, or try-in, is to occur. For example, if the original try-in revealed that the partially cured denture device was an extremely poor fit, then another fit may be performed to determine the accuracy of the denture device after the adjustments have been made based on the new bite registration. However, if the original try-in yielded a substantially close fitting denture device, another try-in may not be required. Thus, if another try-in were not to be performed, process 900 may return to step 922 where a bonding agent may be applied to a base portion of pre-set arch 120.

If, however, another try-in is to occur, process 900 may proceed to step 942. In some embodiments, another coating or another layer of releasing the releasing agent previously used at step 906 may be applied to denture base portion 124 of pre-set arch 120 prior to step 942. After pre-set arch 120 is placed back into channel 402 of partially cured denture base material 400, process 900 may return to step 916, where a test of the fit of the partially cured denture device, now adjusted based on the new bite registration, may be performed by fitting the partially cured denture device in the patient's mouth.

Figure 11:
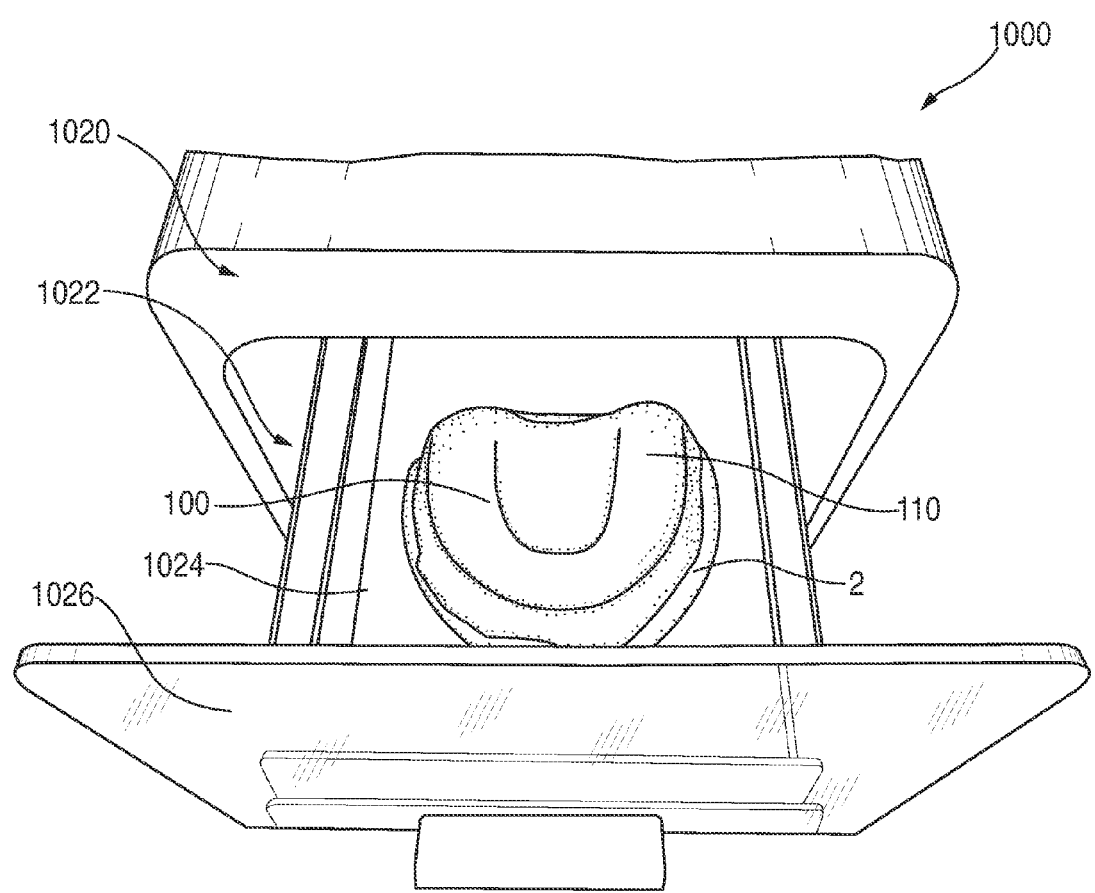
FIG. 11 is an illustrative diagram of an amount of denture base material adapted to a model of a patient's mouth being placed in a curing device in accordance with various embodiments.

FIG. 11 is an illustrative diagram of an amount of denture base material adapted to a model of a patient's mouth being placed in a curing device in accordance with various embodiments. Curing device 1000 may include housing 1020 which may be substantially cube shaped with one side removed. For example, opening 1022 within housing 1020 may allow moveable tray 1024 to be inserted into curing device 1000 and/or remove tray 1024 from housing 1020.

In some embodiments, at an end of moveable tray 1024 is a plastic wall 1026. Wall 1026 may serve multiple purposes. For example, when moveable tray is fully inserted into housing 1020 of curing device 1000, wall 1026 serves as "closing" opening 1022 such that curing device is a substantially closed device. As another example, wall 1026 may be transparent, or substantially transparent, such that an individual may be able to view an object, such as a denture device, placed within curing device 1000 when moveable tray 1024 is inserted. Wall 1026 may, in some embodiments, be made of an UV light blocking plastic, plexi-glass, or acrylic, and may be capable of blocking any UV rays emitted by curing device from exiting curing device 1000 through opening 1022 when wall 1026 closes opening 1022.

In one illustrative, non-limiting embodiment, a dental practitioner may place an uncured amount of denture base material 100 adapted to model 2 of a patient's mouth on moveable tray 1024. The practitioner may then close curing device by pushing tray 1024 into opening 1022 such that wall 1026 encloses curing device 1000. After curing device has been closed, the practitioner may set an amount of time and an intensity of light curing for curing device 1000 such that curing device 1000 may partially or fully cure uncured denture material 100.

Figure 12:
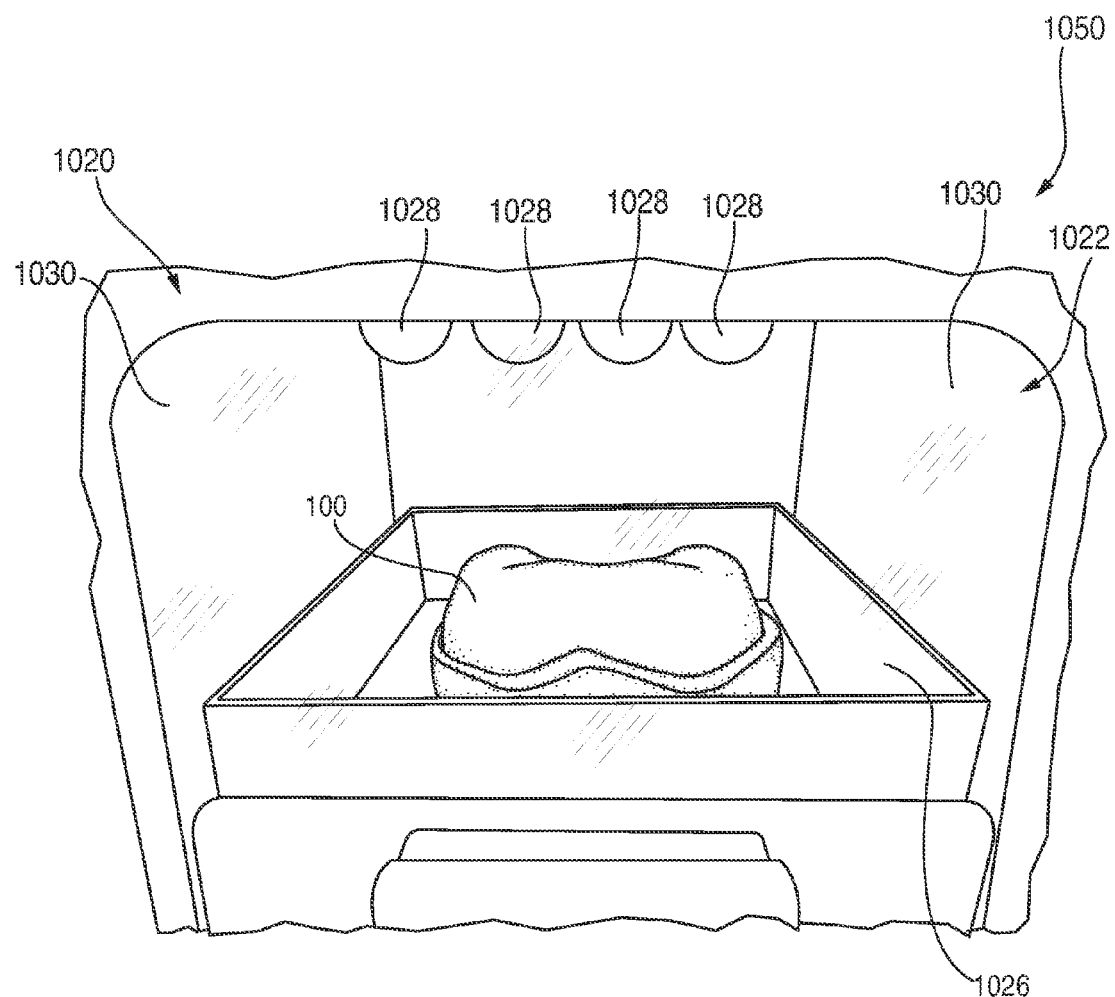
FIG. 12 is an illustrative diagram of a side view of the amount of denture base material adapted to a model of a patient's mouth of FIG. 11 placed within the curing device in accordance with various embodiments.

FIG. 12 is an illustrative diagram of a side view of the amount of denture base material adapted to a model of a patient's mouth of FIG. 11 placed within the curing device in accordance with various embodiments. Side view 1050 of curing device 1000 may include denture base material 100 adapted to model 2 placed inside of opening 1022 of curing device 1000. In this particular scenario, wall 1026 has been closed such that curing device 1000 is a substantially closed device. In some embodiments, one or more inner walls 1030 of housing 1020 may be reflective. For example, walls 1030 located on either side of moveable tray 1024 when inserted into housing 1020 of device 1000 may be made of a reflective material such as glass. Reflective walls 1030 may allow any UV light to be reflected within curing device 1000 such that suitable curing of denture base material 100 occurs.

In some embodiments, curing device 1000 may include one or more curing lights, such as lights 1028. For example, lights 1028 may be UV lights operable to output UV light at a specific intensity for a selected amount of time. In some embodiments, however, lights 1028 may be high intensity white lights, which may be programed to output white light at a desired intensity for any duration of time. Persons of ordinary skill in the art will recognize that the aforementioned are merely examples of curing device 1000, and any suitable curing mechanism, such as light, or air curing, may be used. For example, device 1000 may include one or more vents operable to dry denture base material 100 by removing moisture from within housing 1020.

The above described embodiments of the invention are presented for purposes of illustration and not of limitation.

What is claimed is:

1. A method of fabricating a denture, comprising:
    adapting an amount of an uncured denture base material to a model of a patient's mouth;
    adjusting a pre-set arch of denture teeth to fit the model of the patient's mouth;
    applying a bonding agent to a base denture portion of the pre-set arch of denture teeth;
    impressing the pre-set arch of denture teeth to an occlusal surface of the uncured denture base material to create a channel within the uncured denture base material; and
    curing the uncured denture base material and the pre-set arch of denture teeth to form a substantially unitary denture device.

2. The method of claim 1, wherein adjusting further comprises:
    heating the pre-set arch of denture teeth to at least a first temperature.

3. The method of claim 2, wherein the first temperature is 100 degrees Celsius.

4. The method of claim 1, wherein adjusting further comprises:
    modifying at least one of an arch width, occlusal planes, and amount of base material of the pre-set arch of denture teeth such that the pre-set arch of denture teeth substantially fits the model of the patient's mouth in proper occlusion.

5. The method of claim 1, wherein the bonding agent is methyl methacrylate monomer.

6. The method of claim 1, wherein impressing occurs after the pre-set arch of denture teeth has been positioned over a ridge of the uncured denture base material.

7. The method of claim 1, wherein impressing aligns the pre-set arch of denture teeth in a shape and an orientation for desired denture occlusion.

8. The method of claim 1, wherein the uncured denture base material comprises one of a light-cure denture base material and an auto-polymerizing denture base material.

9. The method of claim 1, further comprising:
    applying, prior to curing, an additional amount of denture base material to at least one of a buccal, a labial, and a lingual seam.

10. The method of claim 1, wherein the denture base material comprises a light-cure denture base material, curing further comprises:
    applying a high-intensity white light to the light-cure denture base material and pre-set arch of denture teeth.

11. The method of claim 1, wherein the denture base material comprises an auto-polymerizing denture base material, curing further comprises:
    allowing the denture base material and pre-set arch of denture teeth to set for an amount of time such that the auto-polymerizing material sets.

12. The method of claim 1, further comprising:
    trimming the substantially unitary denture device to remove any excess denture base material.

13. The method of claim 1, further comprising:
    polishing the substantially unitary denture device to remove any imperfections.

14. A method of fabricating a denture, comprising:
    adapting an amount of an uncured denture base material to a model of a patient's mouth;
    adjusting a pre-set arch of denture teeth to fit the model of the patient's mouth;
    impressing the pre-set arch of denture teeth to an occlusal surface of the uncured denture base material to create a channel within the uncured denture base material;
    performing a first cure to the uncured denture base material and the pre-set arch of denture teeth;
    testing a first cured denture device comprising the first cured denture base material and the pre-set arch of denture teeth to determine if the first cured denture device is formed correctly;

removing, if the first cured denture device has been formed correctly, the pre-set arch of denture teeth from the first cured denture base material;

applying a bonding agent to a denture base portion of the pre-set arch of denture teeth;

pressing the pre-set arch of denture teeth into the channel of the first cured denture base material; and performing a second cure to the first cured denture base material and the pre-set arch of denture teeth to form a substantially unitary denture device.

15. The method of claim 14, wherein the first cure comprises one of a partial cure and a full cure.

16. The method of claim 14, further comprising:
applying a releasing agent to a denture base portion of the pre-set arch of denture teeth prior to impressing.

17. The method of claim 16, wherein if it is determined that the first cured denture device is not formed correctly, the method further comprises:
obtaining a new bite registration of the patient's mouth prior to applying the bonding agent; and
adjusting at least one dimension of the channel within the first cured denture base material or of the pre-set arch of denture teeth based on the obtained new bite registration of the patient's mouth.

18. The method of claim 15, further comprising:
adding an additional amount of uncured denture base material to at least one of a buccal seam, a labial seam, and a lingual seam where the channel and the pressed pre-set arch of denture teeth meet.

19. The method of claim 17, wherein performing the second cure further comprises:
curing the additional amount of uncured denture base material.

20. The method of claim 14, wherein testing further comprises:
determining if the first cured denture device is formed correctly by placing the first cured denture device into the patient's mouth.

\* \* \* \* \*